(12) United States Patent
Deshays et al.

(10) Patent No.: US 10,111,976 B2
(45) Date of Patent: Oct. 30, 2018

(54) METHODS, SYSTEMS, AND DEVICES FOR HIGH-LEVEL DISINFECTION

(71) Applicant: Germitec SA, Clichy (FR)

(72) Inventors: Clément Deshays, Paris (FR); Adrian Edward Smith, Emerald Hills, CA (US); Robert Bruce Chess, Woodside, CA (US); Frédéric Lepine, Saint Gratien (FR)

(73) Assignee: Germitec SA, Clichy (FR)

( * ) Notice: Subject to any disclaimer, the term of this patent is extended or adjusted under 35 U.S.C. 154(b) by 71 days.

(21) Appl. No.: 15/172,075

(22) Filed: Jun. 2, 2016

(65) Prior Publication Data

US 2016/0279275 A1    Sep. 29, 2016

Related U.S. Application Data

(63) Continuation of application No. 14/280,010, filed on May 16, 2014, now Pat. No. 9,364,573.

(Continued)

(51) Int. Cl.
*G01J 1/00* (2006.01)
*G01N 23/00* (2006.01)
(Continued)

(52) U.S. Cl.
CPC .............. *A61L 2/24* (2013.01); *A61B 8/4422* (2013.01); *A61L 2/10* (2013.01); *G01J 1/429* (2013.01); *G01K 13/00* (2013.01)

(58) Field of Classification Search
CPC ..... A61L 2/00; A61L 9/00; A61L 9/03; A61L 9/18; A61L 9/20
(Continued)

(56) References Cited

U.S. PATENT DOCUMENTS 3,764,364 A    10/1973   Seiner
3,956,201 A    5/1976    Seiner
(Continued)

FOREIGN PATENT DOCUMENTS

EP    2 524 606 A1    11/2012
JP    2-504004 A      11/1990
(Continued)

OTHER PUBLICATIONS

Rutala et al. "Guideline for Disinfection and Sterilization in Healthcare Facilities 2008" *The Center for Disease Control*, 158 pages, 2008.
(Continued)

*Primary Examiner* — Monzer R Chorbaji
(74) *Attorney, Agent, or Firm* — Seed IP Law Group LLP

(57) ABSTRACT

A disinfection device includes a disinfection chamber into which a radiation source emits ultraviolet-C (UV-C) radiation. A radiation sensor detects the amount of UV-C radiation within the disinfection chamber, and a temperature sensor produces temperature values of a temperature within the disinfection chamber. A processing unit generates accumulated UV-C radiation values and verifies that the accumulated UV-C radiation value in the disinfection chamber reaches a first radiation threshold while also verifying that the temperature in the disinfection chamber stays below a first temperature threshold. The UV-C radiation may be emitted into the disinfection chamber over one or more fixed periods of time while the total time for the disinfection process is limited to a primary time interval. The process may terminate successfully if the first radiation threshold is exceeded before the primary time interval expires. The disinfection device provides high level disinfection of contaminated articles in a short time and at a low temperature.

20 Claims, 15 Drawing Sheets

Related U.S. Application Data

(60) Provisional application No. 61/824,775, filed on May 17, 2013.

(51) Int. Cl.

| | | |
|---|---|---|
| *A61L 2/00* | (2006.01) |
| *G01N 21/00* | (2006.01) |
| *A61L 2/24* | (2006.01) |
| *A61L 2/10* | (2006.01) |
| *G01J 1/42* | (2006.01) |
| *G01K 13/00* | (2006.01) |
| *A61B 8/00* | (2006.01) |

(58) Field of Classification Search
USPC ...... 422/1, 22, 24, 186; 250/453.11, 455.11, 250/492.1
See application file for complete search history.

(56) References Cited

U.S. PATENT DOCUMENTS

| | | | |
|---|---|---|---|
| 4,475,900 A | 10/1984 | Popovich et al. |
| 4,882,496 A | 11/1989 | Bellotti et al. |
| 6,231,819 B1 | 5/2001 | Morello |
| 7,982,199 B2 | 7/2011 | Deshays |
| 8,313,017 B2 | 11/2012 | Deshays |
| 8,334,521 B2 | 12/2012 | Deshays |
| 8,356,745 B2 | 1/2013 | Deshays |
| 8,623,275 B2 | 1/2014 | Deshays |
| 8,636,950 B2 | 1/2014 | Deshays |
| 8,673,210 B2 | 3/2014 | Deshays |
| 2009/0280035 A1 | 11/2009 | Koudymov et al. |
| 2010/0138234 A1 | 6/2010 | Deshays |

FOREIGN PATENT DOCUMENTS

| | | |
|---|---|---|
| JP | 4-212361 A | 8/1992 |
| JP | 2010-149020 A | 7/2010 |
| WO | 2004/033081 A2 | 4/2004 |
| WO | WO 2004/033081 A2 * | 4/2004 |
| WO | 2007/033212 A2 | 3/2007 |
| WO | 2008/108864 A2 | 9/2008 |
| WO | 2008/108864 A3 | 9/2008 |
| WO | 2012/142427 A1 | 10/2012 |

OTHER PUBLICATIONS

Notification of Reasons for Refusal, dated Jun. 19, 2018, for Japanese Application No. 2016-514141, 11 pages (with machine generated English Translation).

* cited by examiner

METHODS, SYSTEMS, AND DEVICES FOR HIGH-LEVEL DISINFECTION

CROSS-REFERENCE TO RELATED APPLICATIONS

The present application is a Continuation of U.S. patent application Ser. No. 14/280,010, filed on May 16, 2014, which claims the benefit of U.S. Provisional Application No. 61/824,775, filed on May 17, 2013, each of which are hereby incorporated by reference in their entirety.

BACKGROUND

Technical Field

Devices and systems for disinfecting contaminated articles are described herein. Methods for determining operating conditions for the devices and systems described herein, as well as methods for disinfecting contaminated articles, are also provided.

Description of the Related Art

Proper disinfection or sterilization of reusable medical instruments is important in preventing the person-to-person transmission of pathogenic microbes. The level of sterilization and disinfection applied to medical instruments depends on how the device is classified. The Centers for Disease Control (CDC) classifies a medical instrument as a critical item, semi critical item, or noncritical item, depending on the intended use of the device (CDC Guideline for Disinfection and Sterilization in Healthcare Facilities, 2008). In the CDC Guideline, it is stated that critical items confer a high risk for infection if they are contaminated with any microorganism.

Examples of critical items are devices that contact sterile tissue and include surgical instruments, implants, and ultrasound probes used in sterile body cavities. These devices must be sterilized prior to use.

Semi critical items typically contact mucous membranes or non-intact skin. Exemplary semi critical items include such devices as probes used in vaginal, rectal, and urological exams, equipment for respiratory therapy and anesthesia, and certain endoscopes. These medical devices should be free from all microorganisms; however, some small numbers of bacterial spores are considered permissible. Semi critical items require at least high level disinfection (HLD).

Noncritical items are those that come in contact with non-mucous membranes of intact skin (e.g., blood pressure cuffs and stethoscopes). In contrast to critical and some semi critical items, which are often disinfected with large, fixed, disinfection systems, most noncritical reusable items may be decontaminated where they are used to achieve intermediate or low levels of disinfection, and these items typically do not need to be transported to a central processing area for service.

Because critical items confer a high risk for infection when they are contaminated with any microorganism, they are typically subjected to sterilization processes that kill and remove all microorganisms. Similarly, semi-critical items require high-level disinfection (HLD) where population levels of pathogens are reduced to very low levels prior to or between uses. The most common methods for achieving sterilization or high-level disinfection include treatments using high temperature steam and/or chemical disinfectants. Chemical treatments are often used where the article to be treated is heat sensitive, and chemical disinfectants suitable for use in sterilizing or disinfecting medical devices include, for example, glutaraldehyde, hydrogen peroxide, ortho-phthalaldehyde, and peracetic acid with hydrogen peroxide. Currently, the most common methods for achieving high level disinfection of semi-critical medical devices include soaking the devices in a chemical bath. The chemical bath method for semi-critical items may include achieving HLD by soaking for shorter periods of time than would be required to assure complete sterilization.

Although effective, there are disadvantages to sterilization and disinfection processes that utilize steam or chemical treatments. For example, the high temperature associated with steam sterilization can damage the instrument being sterilized. Additionally, the chemicals used for chemical sterilization or disinfection are often costly to store and dispose of properly, and their toxicity can present risks to personnel handling them. Another disadvantage of chemical sterilization is that in many cases, only a portion of an instrument is immersed or otherwise exposed to the chemical solution. Immersing a portion of a medical device in a disinfectant bath commonly treats only that portion of the device, leaving other parts potentially contaminated. Furthermore, chemical methods and high heat (i.e., severe heating to high temperatures in steam) systems can cause degradation of the materials used to make the medical device being treated. Steam- or chemical-based processes can also be time consuming with some procedures taking between 15-40 minutes to complete, and these procedures typically require the instrument or device to be removed to a central location for treatment and then returned to the clinical setting. Such prolonged process times remove medical devices from service, which may be a serious problem if the device is used in an Emergency Department setting. Another problem with removing a medical device from service is related to the installation of the device in the medical setting. Often, medical devices are coupled to central power, communications, or other control equipment. Frequent disconnection and reconnection of medical devices that are tethered to a control unit causes wear and tear and often induces failure at the connector. The cost of implementing containment and safety systems required, in particular those for chemical disinfecting systems (such as fume hoods, dedicated service rooms, and chemical waste systems), makes it difficult in practice for many clinics and small medical groups to employ them. Factors such as these can lead to non-compliance with the sterilization or disinfection procedures for reusable medical devices recommended by the Food and Drug Administration.

BRIEF SUMMARY

Devices and systems that provide effective high level disinfection (HLD) of contaminated articles that are to be reused, doing so in a short time, at a low temperature, and done locally within the clinical setting of use, are described. A disinfection method carried out in a short period of time refers to a method wherein high-level disinfection is achieved within 10 minutes (i.e., 600 seconds or less). The temperature within the disinfection chamber is maintained and monitored at a low level. One temperature that may be monitored is the ambient temperature within a disinfection chamber. In addition, or in the alternative, the surface temperature of the article to be disinfected is monitored. Whether the temperature monitored is a surface temperature of the article being disinfected or an ambient temperature within the disinfection chamber in general, embodiments of the disinfection system are operated such that the temperature does not exceed 35° C. to 55° C.

Though not limited in application to critical and semi-critical medical devices, the disclosed methods, devices, and systems are particularly suited to high-level disinfection of reused medical devices and instruments, including, for example, ultrasound, endotracheal, and other endocavity probes. In particular embodiments, the devices and systems described herein utilize ultra-violet ("UV") radiation to rapidly accomplish high-level disinfection without generating unacceptably high temperatures on the surface of and within the articles being processed. Many medical instruments are comprised of polymeric materials, and it is known that heating of polymers can accelerate potential damage or degradation that may result from exposure to radiation during the disinfection process. Applied use of the systems and methods disclosed herein reduce the likelihood of such damage or degradation.

Embodiments disclosed herein are configured for carrying out methods as described herein and include a disinfection chamber. The disinfection chamber may be provided within a housing having a plurality of sidewalls, a top, and a door providing access to the disinfection chamber. The disinfection chamber itself may also include at least one wall defining an interior volume, and in some embodiments, the disinfection chamber will include a plurality of sidewalls, a base, and a top having an open central portion. Where the method and device utilize UV radiation, the disinfection chamber may include one or more reflective interior surfaces, one or more sources of UV radiation, such as, for example, one or more sources of UV-A, UV-B, or UV-C radiation, and one or more radiation sensors. Reflective materials suitable for use in a disinfection chamber as described herein include, for example, aluminum grand brilliant, polytetrafluoroethylene (PTFE), polyvinyl alcohol (PVA), barium sulfate-containing paints, or combinations thereof. Other materials, for example, the reflective materials disclosed in U.S. Pat. No. 3,956,201 at Col. 2, Lines 56-61 and in the examples of Col. 7, Line 50-Col. 12, Line 2 and in other places and in U.S. Pat. No. 3,764,364 at Col. 2, Line 70-Col. 3, Line 20 and in other places, the contents of which are incorporated herein by reference, may also be employed. In order to facilitate placement and disinfection of articles to be processed within the disinfection chamber, the chamber may also include a suspension assembly for hanging, containing, or otherwise maintaining the article to be disinfected in a desired position within the disinfection chamber.

The disinfection chamber is sized and configured to help achieve disinfection of the articles placed therein within a desirable, and in some cases selectable, period of time. For example, the article to be disinfected, UV radiation source(s), and/or UV radiation sensor(s) may be positioned (e.g., introduced, interposed, suspended, or located) within the disinfection chamber at locations that improve exposure of the article to radiation via controlled transmission of radiation from the sources. Additionally, one or more of the article, direct sources of UV radiation, and indirect sources of UV radiation may be non-stationary during a disinfection cycle. In such embodiments, the disinfection chamber is configured and operated such that one or more of the article, direct source(s) of UV light, and/or an indirect source(s) of UV light is moved (e.g., rotated in one or more planes, raised and lowered, and the like) within the disinfection chamber during a disinfection cycle to better ensure each of the surfaces of the article are exposed to disinfecting levels of UV radiation. The number of UV radiation sources (and their input power and output of UV radiation), the number and positioning of UV radiation sensor(s) within the chamber, and the inclusion or selection of material used for creating one or more reflective surfaces within the disinfection chamber may also be selected to provide a device capable of carrying out a method for disinfecting one or more articles within a selected period of time such that the temperature of one or more aspects of the article does not exceed a targeted maximum temperature. In particular embodiments where multiple radiation sources are used within the disinfection chamber, an article to be disinfected may be positioned preferentially within the disinfection chamber. It may be desired to configure the chamber such that the article is substantially equidistant from each of the radiation sources, and in particular embodiments the disinfection chamber is configured such that the one or more articles to be processed therein can be positioned reproducibly within the chamber, that is, at the same location(s) and orientation for each disinfection cycle to ensure repeatable and predictable exposure, and hence disinfection.

In order to facilitate positioning of articles to be processed within the disinfection chamber, the chamber may also include a suspension assembly for hanging, containing, or otherwise maintaining the article to be disinfected in a selected position and/or orientation within the disinfection chamber. Any suitable configuration for such assembly can be utilized. For example, the assembly may be configured to suspend the article under the influence of gravity from a central portion of the top of the disinfection chamber. In other variations, an attachment mechanism may be provided that removably couples the article to an assembly or wall within the disinfection chamber and/or positions and orients the article within the disinfection chamber. Said attachment system may be applied to or interact with a region on the article that is not targeted for disinfection. For example, on the cable of a probe that is attached to an imaging system, or on a region of an independent (unattached) device that is considered non-critical and thus does not require disinfecting treatment. Even further, an attachment mechanism suitable for use in the disinfection chamber may comprise a pair of, pairs of, or sets of complementary mating elements. Assemblies for maintaining or positioning an article within the disinfection chamber may include components made of UV transparent material so as to restrain the article but not interfere with transmission of the disinfecting UV radiation. Configurations might include a tube, holding forks, or positioning surfaces, and they may be arranged fixedly to receive the article, or they may translate into position or be moveable, for example, in a clamshell manner, so as to come together to capture or trap the article to be disinfected.

Systems according to the present description include a device as described herein that is operated to achieve disinfection of one or more articles. In specific embodiments, the disinfection device is operated according to one or more algorithms useful for controlling and/or monitoring the disinfection device. In such embodiments, one or more contaminated articles are positioned within the disinfection chamber of the disinfection device and exposure of the one or more articles to an environmental condition capable of disinfecting the articles (e.g., exposure to UV radiation) is initiated. Once the disinfection condition is initiated, one or more inputs can be collected and processed according to the algorithm(s). In specific embodiments, systems according to the present description are operated according to one or more algorithms for determining, calibrating, or adjusting one or more of the parameters or system conditions, and to determine whether the point has been reached where the disinfection condition may be terminated (the "termination point" or "point for termination"), or, to extend the process, or for signaling a point at which the disinfection condition must be terminated in order to avoid unwanted damage to the one or more articles being processed. The information processed according to an algorithm utilized by the systems described herein may include, for example, determinations of exposure to a disinfecting condition, the temperature at various locations within the chamber or at the surface of the articles being disinfected, and time over which articles are exposed to a disinfecting condition. Information collected may be processed in ways to ensure accurate measurements are taken e.g., measured UV exposure averaged across multiple sensors, compared to historical values, or incorporated into more sophisticated mathematical models and filters. Additional examples of information that can be collected and then processed by an algorithm utilized in operating a system as described herein include the operational status and/or output of UV radiation sources, status or responsiveness of UV radiation sensor(s), and monitoring other factors that may induce variability in the disinfection conditions over time.

The disinfection system can be operated manually such that one or more operators load the one or more articles within the disinfection device, initiate a disinfection cycle, monitor the system parameters necessary for execution of an algorithm utilized to determine the termination point for the cycle, and terminate the disinfection cycle according to the algorithm. The disinfection system can be operated semi-automated such that one or more of the tasks required for operation, such as, for example, monitoring of the system parameters, application of an algorithm to determine the termination point for a given disinfection cycle, or the termination of a disinfection cycle, is automated. Or the disinfection system can be operated fully automated. For purposes of the present disclosure, a fully automated system is one in which, once a disinfection cycle is initiated by an operator, each of the subsequent steps through termination of the disinfection cycle are automated. In particular embodiments, the systems disclosed herein include one or more processors capable of running one or more algorithms operable to calibrate system components, monitor disinfection conditions, and terminate a disinfection cycle. In some embodiments, the systems described herein include one or more processors configured to run algorithms that assess and/or determine the point of termination for a disinfection cycle based on one or more system conditions. For example, measurements may be taken from one or more sensors throughout the disinfection cycle of at least: 1) a mathematical weighting such as a simple average of—or point exposures to—a disinfecting condition, measured from the one or more sensors, 2) total exposure to a disinfecting condition as measured from one or more sensors, 3) a combination of average exposure to a disinfecting condition measured by one or more sensors considered together with total exposure to the disinfection condition measured at one or more of the plurality of sensors, 4) duration or elapsed time of actual exposure to a to a disinfecting condition, 5) temperature, such as one or more of a temperature measured within the disinfection chamber and one or more surface temperatures at positions of interest on the article subjected to the disinfection cycle, 6) the operating conditions of system components, such as, for example, one of more radiation sources or sensors, and 7) a more sophisticated mathematical process (e.g., filter), such as selectively weighting the exposure of different sensors based on the sensors' position in the chamber, the sensors' proximity to the article, a change in exposure over time detected by the sensors, or some other process.

Methods for rapid, high-level disinfection of contaminated articles are also provided herein. Methods disclosed can be carried out under conditions that are less prone to damage or degrade the one or more articles being disinfected. For example, using UV radiation, methods according to the present disclosure can accomplish high-level disinfection of a medical device in a matter of minutes (e.g., less that 10 minutes), while maintaining conditions such that the surface temperatures of the device(s) being disinfected do not exceed a selected upper threshold, for example, no more than 55° C. In even more specific embodiments, the methods described herein may use UV-C radiation to accomplish the selected high-level of disinfection within a time period considered acceptably short to make the disinfected device available for reuse in the clinical or treatment setting. Reasonable times are from 5 minutes or less, 3 minutes or less, 1.5 minutes or less, and 1 minute or less. The rapid disinfection cycle times provided by methods described herein can lead to improved productivity and compliance with the disinfection protocols, and also avoid undesired thermally accelerated UV (or other radiation) degradation of the articles being disinfected.

The chosen radiation exposure and chosen process temperatures of methods according to the present description serve to mitigate degradation of component materials and or joints or connections between components of the articles being disinfected. The methods, devices, and systems provided are suited to eliminating a range of microorganisms, including, for example, *mycobacterium* species, *Escherichia coli, Staphylococcus aureus, Tricophyton mentagrophytes, Pseudomonas aeruginosa, Enterococcus hirae, Bacillus subtilis, Bacillus cereus, Clostridium sporogenes, Candida albicans*, orthopoxvirus, enterovirus, adenovirus type 5, and human papilloma virus.

Methods for determining acceptable disinfection conditions for a given article, microorganism, or type of contamination are also provided. In order to better identify the conditions required for disinfection and to reduce the potential for undesired over- or under-exposure of articles to disinfection conditions, methods described herein provide for setting and confirming operational parameters of the disinfection devices and systems described herein using test data collected for targeted microorganisms. For example, in specified embodiments, testing of one or more pathogens of interest is conducted, wherein a known amount of selected pathogen(s) (e.g., live bacteria, dormant spores, fungi, molds, viruses) is exposed to a controlled disinfection condition (e.g., a known dose of UV radiation, in energy delivered per unit area). The selected pathogen(s) can be deposited on a substrate, such as a glass substrate, and exposed to UV radiation delivered from a UV source positioned to provide a controlled dose of UV radiation.

A radiation source may be operated such that it delivers radiation energy at a constant rate measured in Joules/second, Watts, or some other unit of measure, and delivers radiation energy for a selected or selectable amount of time (e.g., seconds) to deliver the selected energy dose. (In the study of photonics and radiation, it is customary to define a reference area in $m^2$ or $cm^2$ upon which the radiation impinges, or through which it passes, when defining the power level per unit area, or Irradiance in Watts/$cm^2$). In such embodiments, for example, the target can be irradiated directly from above, with incident radiant energy measured at the plane of the substrate. The conditions required to achieve a certain logarithmic reduction in viable pathogen(s) being evaluated provide starting conditions for setting the system conditions and disinfection cycle times for the disinfection systems described herein. Using such information, the disinfection cycle conditions are then confirmed in the actual disinfection system via one or more test runs with the articles to be disinfected. Depending on the results achieved with the starting conditions, the disinfection conditions can be adjusted up or down to achieve the level of disinfection required without risking unnecessary additional exposure of the target article to the disinfecting conditions.

The devices and systems described herein may be configured to allow calibration of the one or more sources of disinfecting radiation and/or the one or more detectors of disinfecting radiation. For example, the disinfection chamber may be configured to allow for placement of one or more calibrating sensors and assessment of the instant (i.e., at the moment in time the measurement is made) irradiance level and/or total dose of disinfecting radiation energy (i.e., the integral of the irradiance over time) delivered to one or more regions within the chamber. The readings provided by the one or more calibrating sensors can be used to adjust system cycle times and better ensure delivery of a minimum dose of disinfecting radiation energy. The calibrating sensor may be associated with a positioning assembly, and the disinfection chamber may be configured to receive the positioning assembly so that the placement of the calibrating sensor within the disinfection chamber is precise (i.e., repeatable) and accurate (i.e., positioned at the intended location). In particular embodiments, the readings taken by the one or more calibrating sensors are compared to the readings detected by the one or more sensors included in the disinfection chamber. Such a comparison allows the values detected by the one or more calibration sensors to be correlated to the values detected by the one or more sensors included in the disinfection chamber and yielding a calibration function that is applied to the nominal readings coming from the one or more sensors of the disinfection chamber. Calibrating the system in this way enables the system and/or its operator to, for example, establish selected initial operating levels in the system, to re-establish the selected operating levels as the system components age and change with time or after service and/or replacement of components such as radiation sources or detectors, and to account for variation between systems as well as other sources of variability in the amount of disinfecting radiation emitted and detected within the disinfection chamber.

A disinfection device may be summarized as including: a disinfection chamber having an interior volume; at least one radiation source configured to emit ultraviolet-C (UV-C) radiation into the disinfection chamber; at least one radiation sensor configured to detect an amount of UV-C radiation within the interior volume of the disinfection chamber; at least one temperature sensor configured to produce a temperature value representative of at least one temperature within the interior volume of the disinfection chamber; and a processing unit configured to direct operations of the disinfection device, the operations including: generating an accumulated UV-C radiation value, the accumulated UV-C radiation value representing an amount of UV-C radiation detected by the at least one radiation sensor; verifying that the accumulated UV-C radiation value reaches a first radiation threshold; and verifying that the temperature value from the temperature sensor does not reach a first temperature threshold.

A disinfection method may be summarized as including: providing a disinfection chamber having an interior volume, the disinfection chamber arranged to receive ultraviolet-C (UV-C) radiation emitted by at least one radiation source; directing the at least one radiation source to emit UV-C radiation into the interior volume over a fixed period of time that does not exceed a primary-timed-interval; detecting with at least one radiation sensor an amount of UV-C radiation within the interior volume of the disinfection chamber; generating based on values from at least one temperature sensor a temperature value representative of at least one temperature within the interior volume of the disinfection chamber; and verifying that the temperature value does not reach a first temperature threshold during the primary-timed-interval.

A non-transitory computer readable medium having executable software instructions thereon that, when executed, cause a processing unit to operate a disinfection device, may be summarized as including: executing a monitoring algorithm, the monitoring algorithm configured to perform the acts of: receiving an open/closed status indication associated with an access opening to a disinfection chamber of the disinfection device; preventing a radiation source of the disinfection device from emitting radiation based on the open/closed status indication; concurrent with executing the monitoring algorithm, executing a disinfecting algorithm configured to perform the acts of: directing the radiation source to emit UV-C radiation into an interior volume of the disinfection chamber over a fixed period of time; detecting with at least one radiation sensor an amount of UV-C radiation within the interior volume of the disinfection chamber; generating an accumulated UV-C radiation value, the accumulated UV-C radiation value representing an amount of UV-C radiation detected by the at least one radiation sensor; verifying that the accumulated UV-C radiation value reaches a first radiation threshold; and verifying that a temperature value from a temperature sensor does not reach a first temperature threshold.

BRIEF DESCRIPTION OF THE SEVERAL VIEWS OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which:

In FIG. 2A, the disinfection chamber is configured as a rectangular parallelepiped. In FIGS. 2B, 2C, and 2D, the disinfection chambers are configured to be triangular, circular, or double elliptical in shape, respectively.

FIG. 3A shows a top view and FIG. 3B depicts a perspective view.

FIG. 4A shows a top view and FIG. 4B depicts a perspective view.

FIG. 5A shows a top view and FIG. 5B depicts a perspective view.

FIG. 6A shows a top view and FIG. 6B depicts a perspective view.

FIG. 7A shows a top view and FIG. 7B depicts a perspective view.

FIG. 8A shows a top view and FIG. 8B depicts a perspective view.

FIG. 9A shows a top view and FIG. 9B depicts a perspective view.

FIG. 10A shows a top view and FIG. 10B depicts a perspective view.

DETAILED DESCRIPTION

Figure 1:
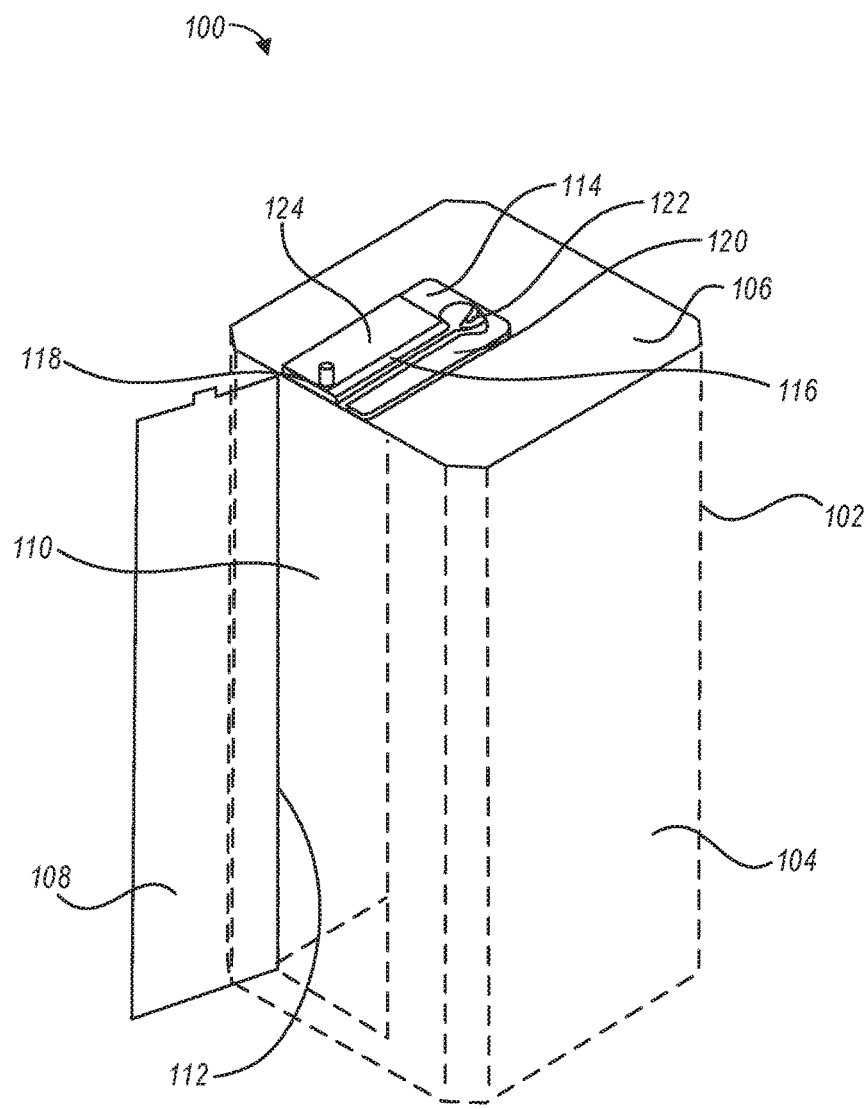
FIG. 1 depicts a perspective view of an exemplary disinfection device.

Devices, systems, and methods for the disinfection of contaminated articles are disclosed herein. The devices, methods, and systems provided are well-suited to the disinfection of medical devices, such as, for example, medical devices classified by the CDC as critical or semi-critical items. Articles processed using the technology described herein may or may not be connected or tethered to another device, system, or component. For example, in the context of a medical device, the technology described herein is suited to the disinfection of ultrasound probes. Currently, many ultrasound probes are tethered to a central processing unit, a display, etc. by one or more cables that provide, for example, power or data communication capabilities to the probe. However, a wireless ultrasound probe need not be tethered to a device, system, or component. The devices, systems, and methods described herein are suited to and can be adapted to accommodate tethered (e.g., wired) devices and untethered (e.g., wireless) devices.

Articles subjected to a disinfection cycle as provided by the methods, devices, and systems described herein receive high-level disinfection. As used herein, "high-level disinfection" and "HLD" refer to a process sufficient to provide a log reduction of at least $10^5$ of one or more specified microorganisms on a contaminated article. HLD disinfection procedures are sufficient to provide log reductions of one or more specified microorganisms of between about $10^5$ to about $10^6$, and in certain embodiments, "high-level disinfection" disinfection procedures provide a log reduction in one or more specified microorganisms of greater than $10^6$ in the article. However, in some instances, the disinfection cycles disclosed herein are sufficient to achieve at least a $10^6$ log reduction of a microorganism on the article. The reduction required in the amount of microorganisms on the article may vary according to the level of disinfection needed, and the level of disinfection provided can be adjusted by varying or adjusting the parameters of the disinfection cycle.

I. Devices & Systems

The devices described herein include a disinfection chamber. The disinfection chamber includes one or more walls that define an interior volume into which an article to be disinfected can be introduced. In some embodiments, the disinfection chamber includes one or more sidewalls, a base, and a top having a central portion. In some embodiments, the interior of the disinfection chamber will generally include one or more reflective surfaces. Where one or more reflective surfaces are provided, such surfaces may be positioned at, near, or extending over at least a portion of the one or more walls. Additionally, one or more reflective surfaces may be positioned relative to one or more sources of disinfecting radiation to facilitate delivery of a selected intensity of disinfecting radiation within the disinfection chamber. In some embodiments, the disinfecting radiation is ultraviolet (UV) radiation generated by a UV tube, and one or more reflective surfaces are positioned totally or partially behind the tube to direct UV radiation generated by the UV tube into a central or disinfecting region of the disinfection chamber. The disinfection chamber may optionally include a suspension assembly for positioning an article to be disinfected within the chamber. The disinfection chamber may be contained within a housing of any suitable shape or geometry that helps to provide disinfection rapidly and at a low temperature. In certain embodiments, the housing containing the disinfection chamber will substantially have the same exterior shape as the disinfection chamber. However, where a housing is provided, the housing can take on any selected shape and size to contain or otherwise support the disinfection chamber and adapt a disinfection system as described herein to a selected application or operating environment.

Generally speaking, high-level disinfection of an article is achieved when UV radiation of homogeneous intensity is delivered to all surfaces of the article more or less equally regardless of the size and shape of the article. To this end, one or more components and features of the disinfection device may be selected to cooperate with the size and shape of articles to be disinfected. The components and features selected include the size and shape of the disinfection chamber; the number and placement of one or more associated radiation sources; the wavelength and power of the radiation source(s); and the position, size, material, and shape of one or more reflective surfaces, one or more partitions, one or more positioning devices, one or more sensors, and one or more other features located within a disinfection chamber. The selections made for a particular disinfection device promote homogeneous dispersion of UV energy within the disinfection chamber, reduce sensitivity to shadowing, and improve uniformity of UV exposure of the article to be disinfected.

The disinfection chamber includes or is arranged to include one or more UV radiation sources and one or more UV radiation sensor assemblies. In specific embodiments, the UV radiation sources within the disinfection chamber are UV-C radiation sources, and the one or more UV radiation sensor assemblies are suited to the detection and quantification of UV-C exposure. The disinfection chamber interior is generally sized and shaped for rapid, high-level disinfection of a contaminated article, and the one or more UV-C radiation sources and one or more UV-C radiation sensors are configured within the disinfection chamber to rapidly achieve high level disinfection of a contaminated article positioned within the chamber.

Figure 2B:
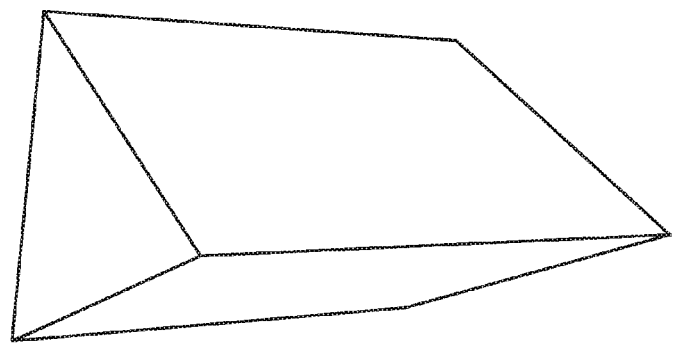
FIGS. 2A-2D show various exemplary disinfection chamber geometries.
Figure 2A:
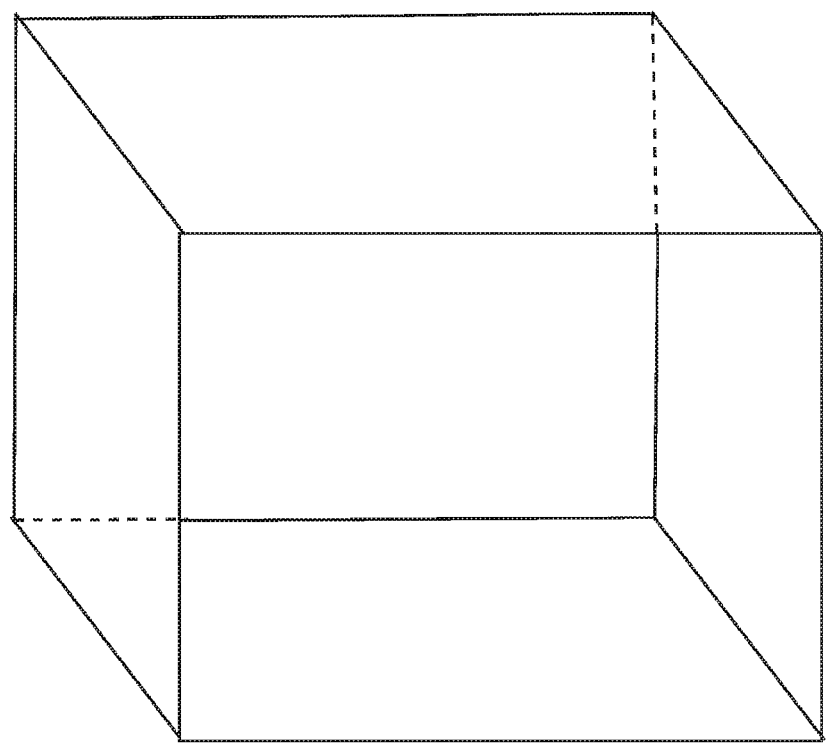

In some embodiments, the cross-sectional shape of the disinfection chamber may take the form of a rectangular parallelepiped (FIG. 2A), a triangle (FIG. 2B), a circle (FIG. 2C), an ellipse, a double ellipse (FIG. 2D), or some other form. The housing and the disinfection chamber may have the same or different general shape or geometry. Referring to FIG. 1, a high-level disinfection is shown having a housing 102 shaped as an octagonal parallelepiped. The housing 102 has a plurality of sidewalls 104, a top 106, and a door 108 disposed within one of the sidewalls for accessing the disinfection chamber 110. Although the door 108 in FIG. 1 is shown as being rotatably movable about a vertical axis, other door configurations may be used, so long as they provide adequate access to the disinfection chamber. It is understood that upon opening door 108, an access opening 112 is created in the disinfection chamber sidewall, and the access opening 112 communicates with the disinfection chamber 110.

The interior of the disinfection chamber may include one or more reflective surfaces arranged to facilitate rapid and low temperature disinfection. The reflective surface is typically formed from one or more materials having at least 30% reflectivity. By "at least 30% reflectivity," it is meant that no more than 70% of the incident UV radiation, particularly in the UV-C range, will be absorbed, and the rest of the incident radiation will be reflected via one or both diffuse and specular reflection. Reflective materials that may be particularly useful in a disinfection chamber include, but are not limited to, aluminum, glass, magnesium, stainless steel, polytetrafluoroethylene, polyvinyl alcohol, substrate materials treated with barium sulfate-containing paints, and alloys, derivatives, and copolymers thereof. In some variations, the reflective surface comprises aluminum, polished to a "grand brilliant" condition. In other variations, the reflective surface may be formed using polytetrafluoroethylene PTFE, or PTFE and similar polymers may be coated by various means onto another substrate, to form the reflective surface. In particular embodiments, the reflective interior surfaces of the disinfection chamber are formed to be as reflective as available manufacturing techniques provide. Such an approach facilitates disinfection processes that utilize high intensity disinfection radiation carried out at low temperatures.

The interior surfaces of the disinfection chamber may be positioned and shaped to reduce the absorption of UV radiation by the interior surfaces and instead reflect and redirect the UV radiation within the disinfection chamber and onto the one or more articles positioned within the chamber. The material choice and configuration of the disinfection chamber may be selected to promote preferential extinction of certain UV or other wavelengths of electromagnetic energy that can contribute to increased temperatures within the disinfection chamber (i.e., longer wavelengths of radiation). That is, the shape of the disinfection chamber may contribute to the intensity and homogeneity of the irradiance established in the chamber, and thus the quick and efficient direction of radiation to the target article (i.e., the radiation passing through the middle of the interior volume of the disinfection chamber), and the reflective material(s) employed in the disinfection chamber may contribute to the reflection (e.g., re-radiation or re-emission) of radiation with low loss (i.e., approximately the same amount of energy returns from the surface as was incident). In particular embodiments, the interior walls of the disinfection chamber are constructed and configured to provide low loss of UV-C radiation emitted from the one or more UV radiation sources. Such embodiments increase the likelihood that UV-C radiation useful for disinfection will be reflected one or more times inside the chamber until the radiation impinges upon the article to be disinfected. In this way, for a given amount of total radiative energy released into the chamber from the source or sources, which also may include some amount of infrared or heat energy, an improved utility is made of the useful UV-C band energy in disinfecting the target device or instrument, while reducing the amount of thermal heating of the target.

As detailed herein, the disinfecting radiation utilized can be UV-C radiation, and in embodiments that utilize UV-C radiation, the one or more radiation sources may be any commercially available device suitable for emitting sufficient UV-C radiation to carry out high-level disinfection. Where one source of UV-C radiation is provided in the disinfection chamber, that source will emit sufficient UV-C radiation to establish an intense radiation field capable of carrying out high-level disinfection as detailed herein. Where two or more sources of UV-C radiation are included in the disinfection chamber, the UV-C radiation sources may include one or more sources of UV-C radiation capable of emitting sufficient UV-C radiation to carry out high-level disinfection. Alternatively, in embodiments of the disinfection chamber that include two or more UV-C sources, such sources may each, on their own, emit insufficient UV-C radiation to achieve high-level disinfection, but when the individual outputs of UV-C radiation emitted from the two or more sources are combined, the total output of UV-C radiation is sufficient achieve high-level disinfection.

In further variations, a remote source of UV-C radiation, such as a standard laser, or solid state laser photodiode, may be employed as a source of disinfecting energy, along with appropriate optical conductors and couplers to cooperate with the light source such that UV-C radiation is introduced into the disinfection chamber. Further, in some embodiments a direct or conducted source of UV radiation could be steered, via a mirror or other device, or scanned along the target. In other embodiments, the target may be moved past a stationary emission region. The target or radiation source may rotate or move in some other way with respect to the other, to provide preferential exposure of the target to the UV radiation.

Though the devices, methods, and systems provided herein are primarily described with reference to UV-C radiation as the disinfecting radiation within the disinfection chamber, the radiation or energy used in the disinfection devices may also be or include UV-A radiation, UV-B radiation, or even non-UV radiation alone or in combination. It is to be further understood that, within the disinfection chamber, exposure of the articles to UV radiation may be carried out in a variety of ways, including combinations of exposure methods.

Instead of UV radiation, such as UV-C radiation, some variations of the devices described herein may use a flash (e.g., pulse) source of energy. A flash source of energy emits very high intensity disinfecting radiation for relatively short intervals. The flash source of energy can provide high-level disinfection of contaminated one or more articles in an acceptably short period of time, and again can reduce the amount of thermal energy related heating within the chamber and on or within the target object. In certain embodiments, a flash source of energy may deliver disinfecting radiation to the one or more articles at such a high rate that high-level disinfection is achieved in period of time selected from 10 seconds or less, 5 seconds or less, 3 seconds or less, and 2 seconds or less. A flash source of energy as contemplated herein may be selected to deliver any selected disinfecting radiation. For instance, a disinfection system as described herein may include a flash source of energy that emits electron beam, gamma-ray, x-ray, gas-plasma, or UV-C radiation. In some embodiments, a flash source of energy delivers a series of on-off pulses. The pulses may have uniform "on" times or varied "on" times, uniform frequencies or varied frequencies, and uniform power or varied power. The total "on time" of the one or more radiation sources and the power level established during the on time will define the total energy delivered into the disinfection chamber. In these embodiments, the energy may be delivered in a short cumulative time but over a longer treatment time (e.g., 60-100 seconds). One advantage of employing a flash energy source is that a reduced amount of thermal heat energy may be released into the chamber. Consequently, the opportunity for heat to build up, for convective and radiative heat transfer mechanisms to establish themselves, and for heat energy to be delivered to the article being disinfected is reduced.

Where a flash source of energy is used, one source of disinfecting radiation may be all that is needed in the disinfection chamber. In such embodiments, to achieve generally homogeneous or uniform radiation exposure on the target article, the radiation emitted by the flash source may first strike a surface that will spread and distribute the radiation before hitting the target. In this case, the target will receive primarily indirect rather than direct, illumination. In other words, the device could be configured so that the source is in a different part of the device than the target. Since the energy spectrum emitted by some types of flash sources may be broader than desired, it may be helpful to filter the energy emitted from the source so only the spectrum of interest is allowed to pass to the disinfection chamber. The filter may serve to minimize the presence of infrared energy, which does not disinfect but will otherwise heat the chamber and raise its temperature. Said filters may also be useful when implemented with the other radiation sources mentioned herein. Combinations of disinfection energy sources may be used in the devices and systems described herein. Where two or more different disinfection energy sources are used, they may be applied sequentially, in parallel, or in various combinations and orders. The inclusion and use of two or more different sources of disinfecting energy may prove advantageous in situations where certain pathogens are more susceptible to a particular source of disinfection energy, and in order to reduce overall exposure of the target article it may be useful to employ a variety of radiations sources, durations, and doses to achieve acceptable disinfection for pathogens of interest.

Where the devices and systems described herein utilize UV radiation, such as UV-C radiation, the UV radiation source(s) and/or the UV radiation sensor(s) are positioned within the disinfection chamber in a manner that facilitates rapid, low temperature disinfection, and in general, the configuration of the disinfection chamber, the sources of disinfecting radiation, and the sensors detecting disinfecting radiation will be selected to provide and confirm a selected exposure of the one or more articles to radiation and/or optimize transmission of radiation from the source(s) to efficiently and reproducibly target an article. As described, a disinfection chamber according to the present description may include a single source of disinfecting radiation, such as one UV-C radiation source. In such embodiments, the radiation source may be positioned on a top or bottom of the chamber. Alternatively, depending on the positioning of the articles to be disinfected, the single radiation source may be positioned on a side of the disinfection chamber or, where the disinfection chamber includes multiple sides, at an intersection formed at an intersection of two sides. However, the devices and systems described herein are not limited to disinfection chambers having a single source of disinfecting radiation.

The disinfection chamber included in the devices and systems according to the present description may utilize multiple radiation sources, of the same or different variety, and different embodiments of a disinfection chamber having multiple sources of disinfecting radiation are detailed herein and illustrated in the accompanying figures. Such embodiments may be advantageous where the surface of the one or more articles to be disinfected is more complex than a single flat surface. For example, an article to be disinfected, such as an endotracheal probe or an ultrasound probe, may have two or more of a front, back, lateral, and dorsal and/or ventral surface that require disinfection. In such a scenario is may be difficult to deliver high intensity radiation to each surface of article with a single source or type of disinfecting radiation. Accordingly, in some embodiments of the disinfection devices described herein, the radiation sources and other structures are arranged to disinfect one particular type of target. That is, the sources and/or other structures may provide illumination to each surface of the specific target, but the device would not function effectively if a different type of target was placed in the disinfection chamber.

Radiation sources that may be employed in devices and systems as described herein are available in the art, and include, for example UV-C emitting lamps. UV-C emitting lamps, also referred to herein as "tubes," are available commercially from various sources, including Philips Lighting B.V., and can be obtained in different shapes, sizes, input energy, and UV-C output ratings. Suitable UV-C tubes for use as a UV-C energy source include low-pressure mercury vapor discharge lamps. However, the disinfection chambers are not limited to a particular UV-C source. Any source capable of emitting UV-C light within the selected UV-C wavelength at an output rating that contributes to the disinfection of a contaminated article could be used in the devices disclosed herein. For example, in addition to or as an alternative to one or more UV-C tubes, a laser or photodiode designed to emit UV-C light may be used to deliver disinfecting radiation within the disinfecting chamber. In particular embodiments, the one or more sources of UV-C radiation included in the disinfection chambers described herein provide a total UV-C output within the chamber that is selected from one of at least 5 Watts of radiant power. For example, the one or more sources may be selected to provide a total UV-C output within the chamber selected from at least 10 W, at least 15 W, at least 20 W, at least 25 W, at least 30 W, at least 40 W, at least 50 W, at least 75 W, at least 90 W, and at least 100 W of radiant power. Where UV-C sources are used as the one or more sources of disinfecting radiation, the frequency band of UV-C light emitted from the one or more sources may be selected from between about 240 nm and about 270 nm and between about 255 nm and about 265 nm.

A disinfection chamber as described herein may be configured to create one or more disinfection regions within the chamber. In such embodiments, the disinfection chamber and/or one or more articles to be disinfected can be further configured to ensure the one or more articles to be disinfected are positioned within the one or more disinfection regions. As used herein, the term "disinfection region" refers to a region within the disinfection chamber wherein a threshold level of high-intensity disinfecting radiation is delivered over the course of a disinfection cycle. In specific embodiments, the disinfection chamber includes one or more sources of UV-C radiation, and the one or more sources of UV-C radiation are selected and arranged to deliver UV-C radiation to one or more disinfecting regions at a minimum irradiance (also referred to as "power") of at least about 1,500 $\rho W/cm^2$. As noted herein, in specific embodiments, the one or more sources of UV-C radiation may be selected to emit UV-C light within a band selected from between about 240 nm and about 270 nm and between about 255 nm and about 265 nm. For example, one or more UV-C source(s) may be selected and arranged such that one or more disinfection regions are formed within the disinfection chamber, and the minimum irradiance of the UV-C radiation delivered to the one or more disinfecting regions is between about 1,500 $\rho W/cm^2$ and about 5,000 $\rho W/cm^2$. In further embodiments, the one or more UV-C source(s) may be selected and arranged to provide one or more disinfecting regions wherein the minimum irradiance of the UV-C radiation delivered within the disinfection region(s) is selected from between about 1,500 $\mu W/cm^2$ and about 2,000 $\mu W/cm^2$, between about 1,500 $\mu W/cm^2$ and about 2,500 $\mu W/cm^2$, between about 1,500 $\mu W/cm^2$ and about 3,000 $\mu W/cm^2$, between about 2,000 $\mu W/cm^2$ and about 2,500 $\mu W/cm^2$, between about 2,000 $\mu W/cm^2$ and about 3,000 $\mu W/cm^2$, between about 2,000 $\mu W/cm^2$ and about 3,500 $\mu W/cm^2$, between about 2,000 $\mu W/cm^2$ and about 2,500 $\mu W/cm^2$, between about 2,000 $\mu W/cm^2$ and about 2,750 $\mu W/cm^2$, between about 2,500 $\mu W/cm^2$ and about 2,600 $\mu W/cm^2$, between about 2,500 $\mu W/cm^2$ and about 2,750 $\mu W/cm^2$, and between about 2,500 $\mu W/cm^2$ and about 3,000 $\mu W/cm^2$, or between other like values.

In some embodiments, a disinfection region created within the disinfection chamber is not only characterized by a minimum irradiance within the region, but may also be characterized by delivery of disinfecting radiation at a substantially uniform irradiance within the region. As used herein in reference to a disinfecting region, the term "substantially uniform" refers to a region within which the irradiance of the disinfecting radiation does not vary by more than 30% within the entire region (i.e., the irradiance measured within the region does not vary by more than 30%). In particular embodiments, "substantially uniform surface irradiation" refers to a disinfecting region wherein the intensity at which the disinfecting radiation is delivered to the surface(s) of the article to be disinfected does not vary across any portion of those surface(s) by more than an amount selected from ±30%, ±25%, ±20%, ±15%, ±10%, and ±5% or another like value.

The one or more walls defining the interior volume of the disinfecting chamber may also be configured to work in conjunction with the one or more sources of disinfecting radiation to deliver high intensity disinfecting radiation to the one or more articles to be disinfected. For example, the one or more walls included in the disinfection chamber and, where included, the one or more reflective surfaces can be configured to function in conjunction with the one or more sources of disinfecting radiation to provide one or more disinfection regions. In some embodiments, the interior volume of the disinfection chamber is defined by one or more sidewalls with a top and/or a bottom wall. In such embodiments, sources of disinfecting radiation can be positioned on or within any sidewall, top wall, bottom wall, or at any junction between any of two or more sidewalls, a sidewall and a bottom wall, and a sidewall and a top wall. The one or more walls defining the interior volume of the disinfection chamber can provide any one of many cross-sectional shapes for the chamber. For example, in particular embodiments, the one or more walls are configured to provide an interior volume having a circular or multi-sided cross section, such as a rectangular, triangular, hexagonal or octagonal cross section. In some embodiments, the disinfection chamber is configured such that the interior volume is defined by a plurality of walls and the cross-sectional shape of the interior volume is a rectangular parallelepiped or octagonal parallelepiped. In still other embodiments the disinfection chamber, or portions thereof, may be shaped as a circle, a parabola, a double ellipse, or some other shape. In some cases, interior walls of the disinfection chamber may be added, removed, or alternatively or in addition re-positioned so that a disinfection chamber having an interior volume defined by a first cross-sectional shape is modified to have an interior volume defined by a second, different cross-sectional shape.

Embodiments of the disinfection chamber may include a reflector totally or partially behind the one or more disinfecting radiation source(s), and in such embodiments, where the source of disinfecting radiation emits UV radiation and is a line source, such as, for example, a tube that emits UV-C radiation, the reflector may be parabolic, with the UV-C radiation source at or near its focus. Such a configuration can result in sending light out from the parabolic reflector in mostly parallel rays. Of course other reflector geometries, UV radiation source locations, and resulting radiation fields are possible. Where tubes emitting UV-C radiation are used as the one or more sources of disinfecting radiation, in some embodiments, the input power delivered by the driving electronics to power the tubes may range from about 20 W to about 200 W. In specific embodiments, the input power for UV tubes used in a disinfection chamber as described herein may be selected from, for example, 20 W, 25 W, 30 W, 35 W, 40 W, 45 W, 50 W, 55 W, 60 W, 65 W, 70 W, 75 W, 80 W, 85 W, 90 W, 95 W, and 100 W or another like value.

One or more sources of disinfecting radiation may be positioned around the one or more sidewalls of the disinfection chamber in a manner that results in radiation of a selected intensity (such as, e.g., energy of an intensity as described in relation to the disinfection regions) being delivered to the one or more articles to be disinfected. The one or more sources of disinfecting radiation can be positioned around the disinfection chamber to provide a disinfection region wherein an article being disinfected receives a threshold level of irradiance of disinfecting radiation over all of the contaminated surfaces of the article that are to be disinfected. For example, in embodiments of the disinfecting chamber having one or more sidewalls, two or more sources of disinfecting radiation, such as two or more sources of UV-C radiation may be positioned along one or more of the sidewalls at uniformly spaced locations. In embodiments having multiple sidewalls, one or more sources of disinfecting radiation may be positioned at one or more corners of the sidewalls. Where the disinfection chamber includes at least one top or bottom wall or surface, one or more sources of disinfecting radiation can be positioned at a top and/or bottom wall or surface to provide a targeted threshold level of irradiance of disinfecting radiation with one or more disinfection regions formed within the chamber. In specific embodiments, where the interior volume of the disinfection chamber is configured to include two or more sidewalls and a bottom wall, with a UV radiation source at each corner formed between the sidewalls and at least one UV radiation source positioned at the bottom wall, the input power of each corner tube may be at least 50 W, and where included, the power of the bottom one or more tubes may be at least 30 W.

Various different configurations of the disinfection chamber are illustrated in FIGS. 1-10B. For example, FIG. 2C illustrates a disinfection chamber 200 with a circular cross section. As shown in FIG. 2C, when the disinfection chamber 200 has an interior volume cross-section shaped as a circle, the UV-C radiation sources 202 may be positioned so that they are spaced equidistant from each other around the periphery of the circle. In the disinfection chamber illustrated in FIG. 2C, a disinfecting region is produced in the central region of the chamber, and the target article, e.g., ultrasound probe 204, is disposed in the center of the circle formed by the wall of the chamber.

Figure 2D:
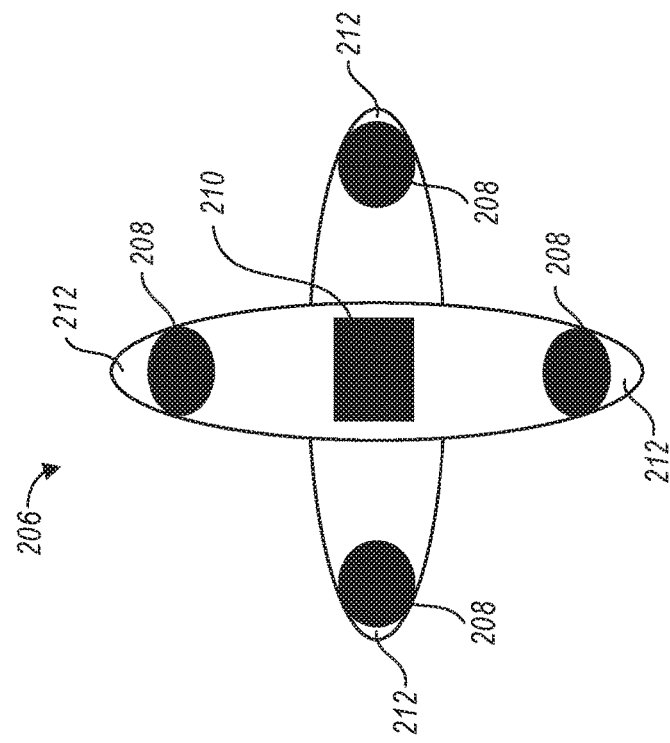
Figure 2C:
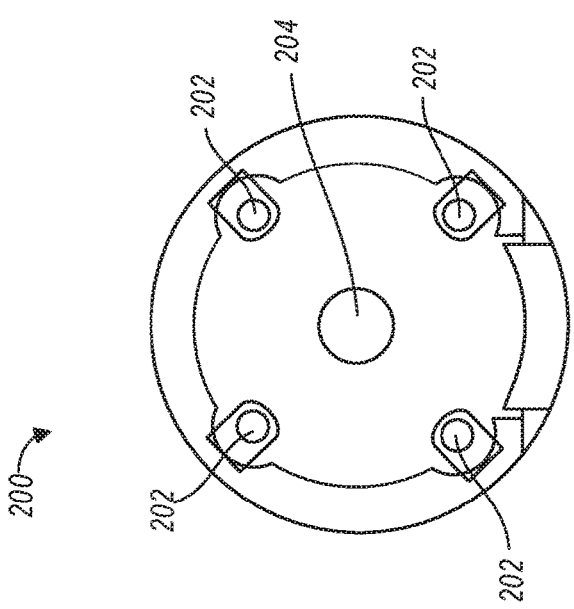

Referring to FIG. 2D, when the disinfection chamber 206 is shaped as a double ellipse, the UV-C radiation sources 208 may be positioned at each vertex 212. The target article, ultrasound probe 210, is disposed in the area where the two ellipses overlap one another.

Figure 3A:
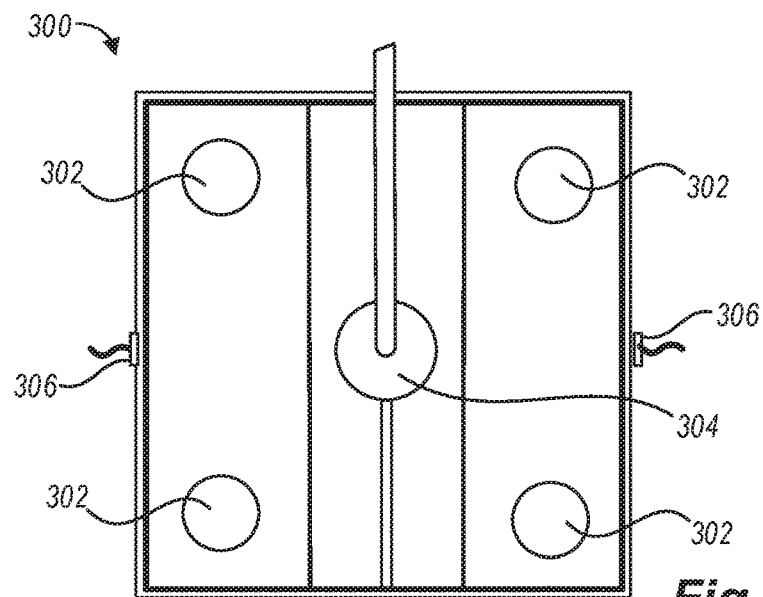
FIGS. 3A-3B are simplified views that show the position of UV-C radiation sources and UV-C radiation sensors within a rectangular parallelepiped disinfection device according to one variation.
Figure 3B:
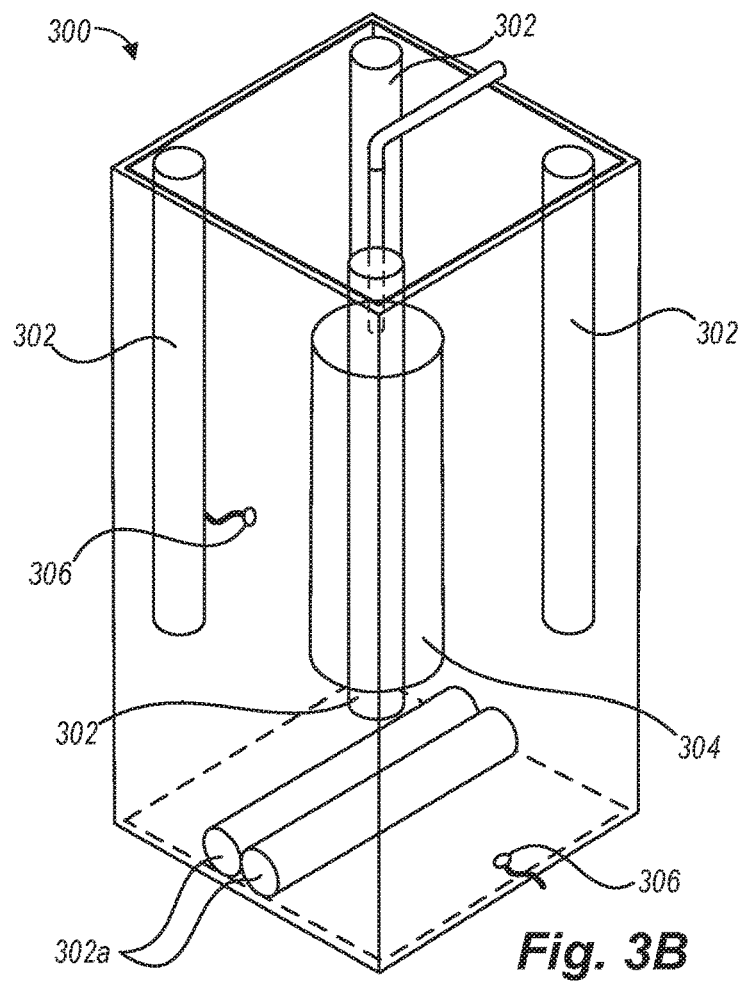

FIGS. 3A-3B illustrate a disinfection chamber 300 that has an interior volume cross-section shaped like a rectangular parallelepiped. In such a configuration, as shown in FIGS. 3A-3B, the UV-C radiation sources 302 may be configured so that one of four sources is positioned in each corner of the chamber to surround the target article, e.g., ultrasound probe 304, and two sources 302a are positioned on the bottom of the chamber under the target article, e.g., ultrasound probe 304. One or more radiation sensors 306 are positioned to measure radiation within the interior volume of the disinfection chamber 300. In cases where two or more radiation sensors 306 are included, the radiation sensors 306 may be cooperatively positioned to measure the radiation in different parts of the disinfection chamber 300. In some cases, multiple radiation sensors 306 are placed in close proximity to each other such that data collected from the plurality of radiation sensors may be compared to indicate that the collected data is valid and the disinfection chamber 300 is operating normally. Some rectangular parallelepiped variations may include only one source on the bottom of the chamber.

Figure 4A:
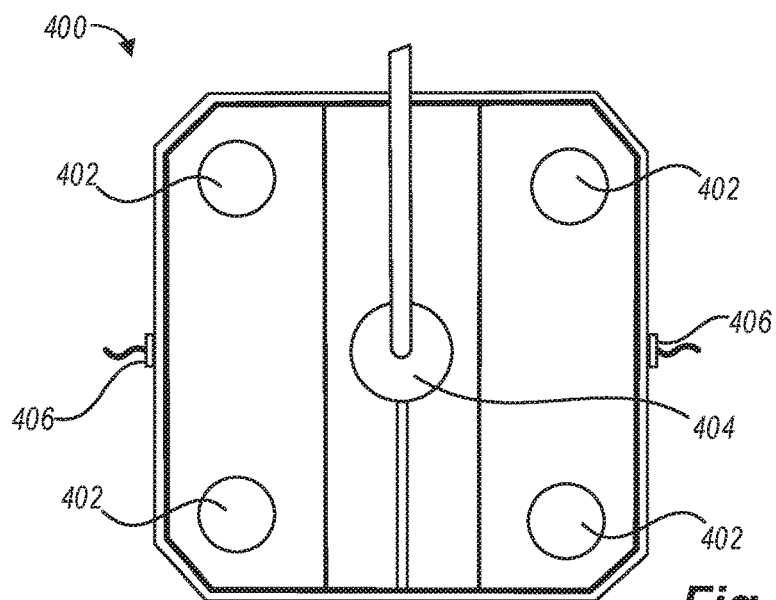
FIGS. 4A-4B are simplified views that show the position of UV-C radiation sources and UV-C radiation sensors within an octagonal parallelepiped disinfection device according to FIGS. 3A-3B.
Figure 4B:
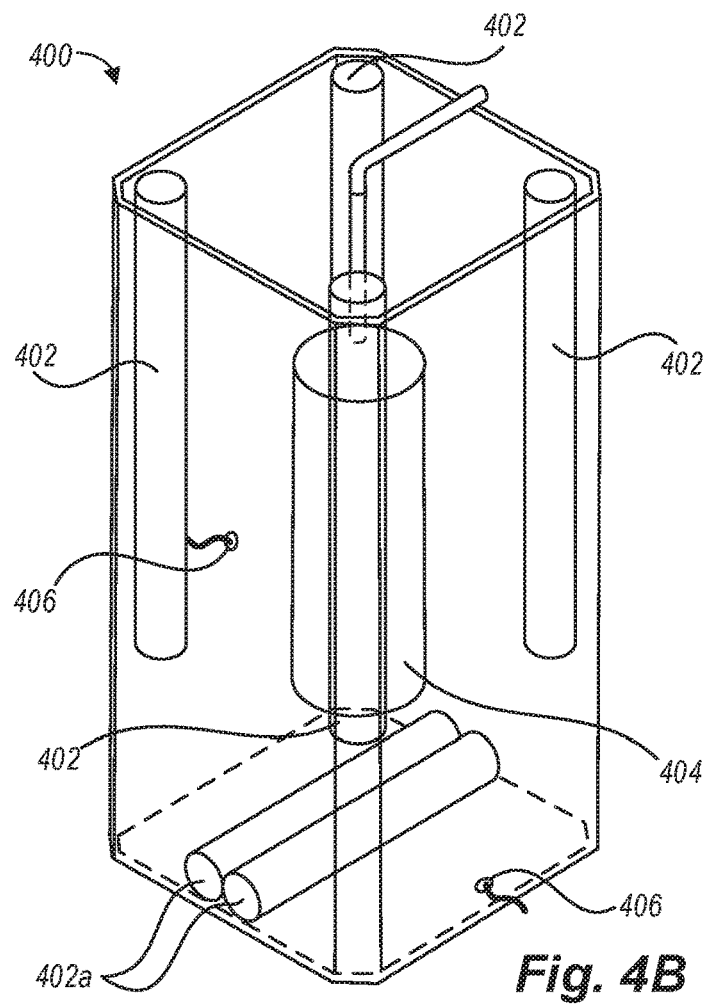
Figure 5A:
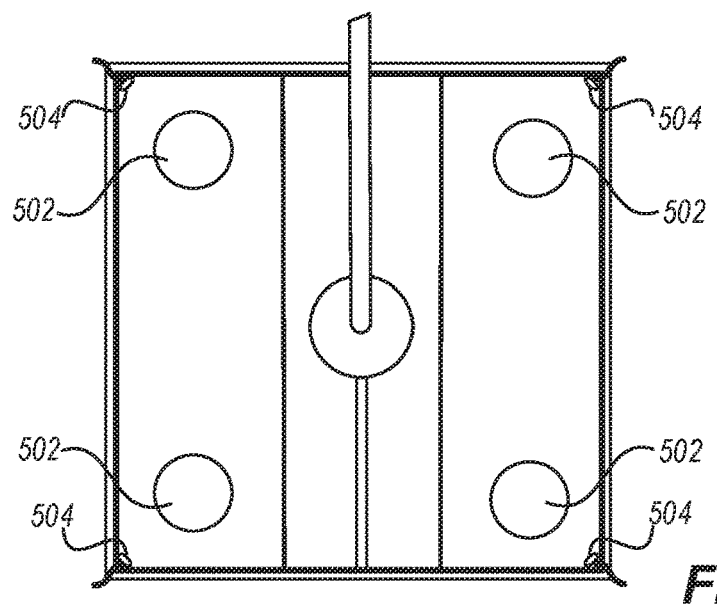
FIGS. 5A and 5B are simplified views that show the position of UV-C radiation sources and UV-C radiation sensors within a rectangular parallelepiped disinfection device according to another embodiment.
Figure 5B:
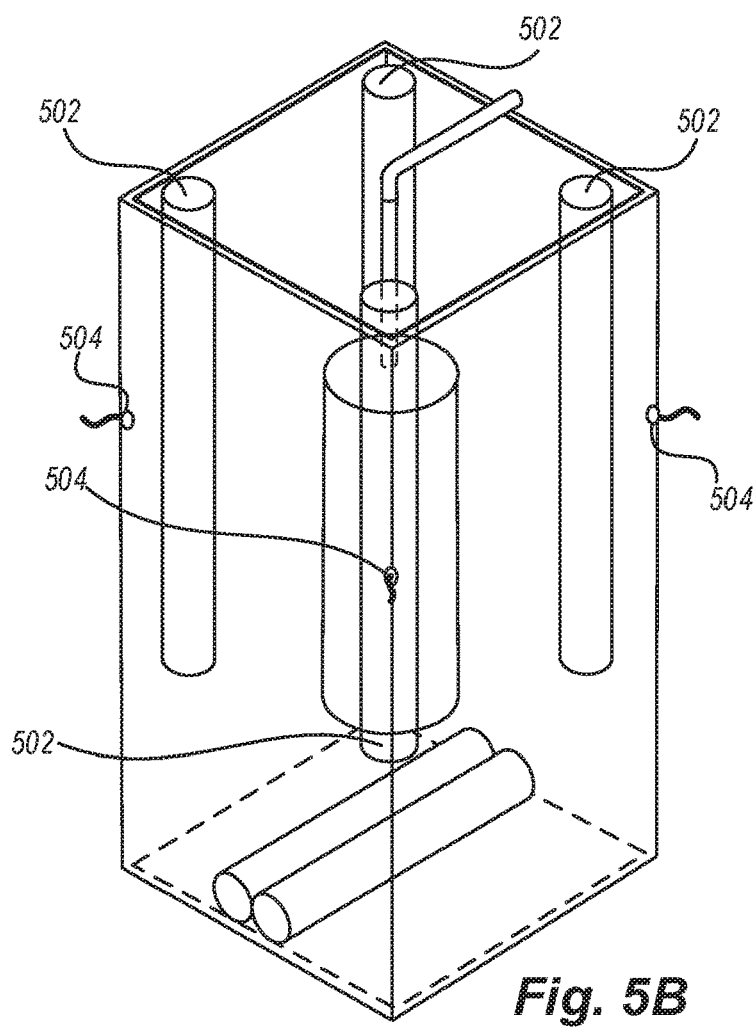
Figure 6A:
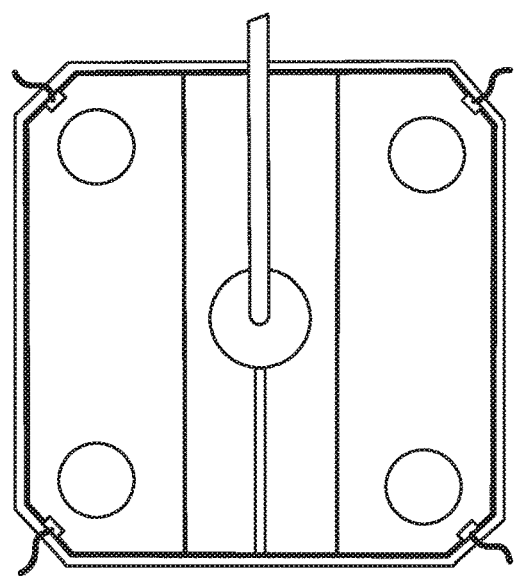
FIGS. 6A and 6B are simplified views that show the position of UV-C radiation sources and UV-C radiation sensors within an octagonal parallelepiped disinfection device according to FIGS. 5A-5B.
Figure 6B:
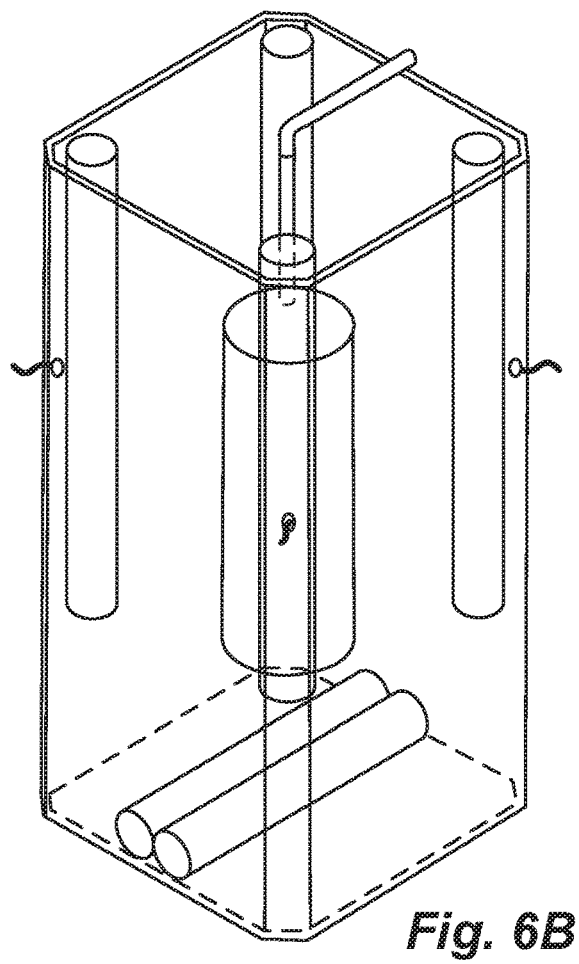
Figure 7A:
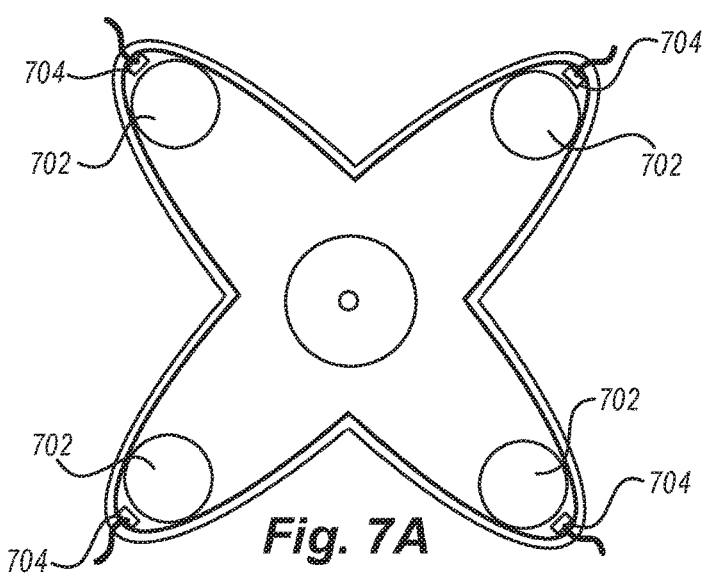
FIGS. 7A and 7B are simplified views that show the position of UV-C radiation sources and UV-C radiation sensors within a double elliptical disinfection device according to another variation.
Figure 7B:
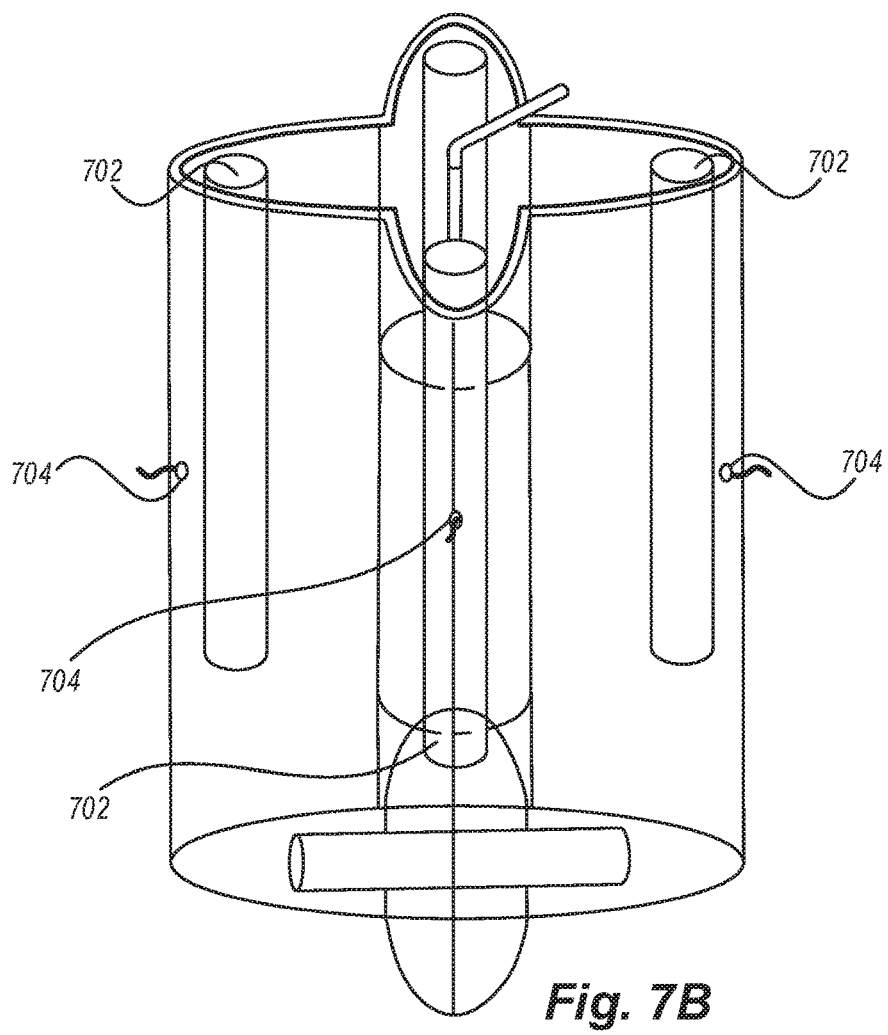
Figure 8A:
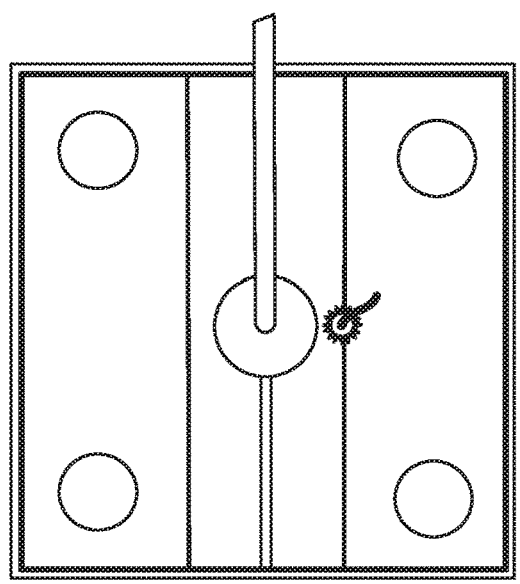
FIGS. 8A-8B are simplified views that show UV-C radiation sources and fiber optic UV-C radiation sensors within a rectangular parallelepiped disinfection device according to another variation.
Figure 8B:
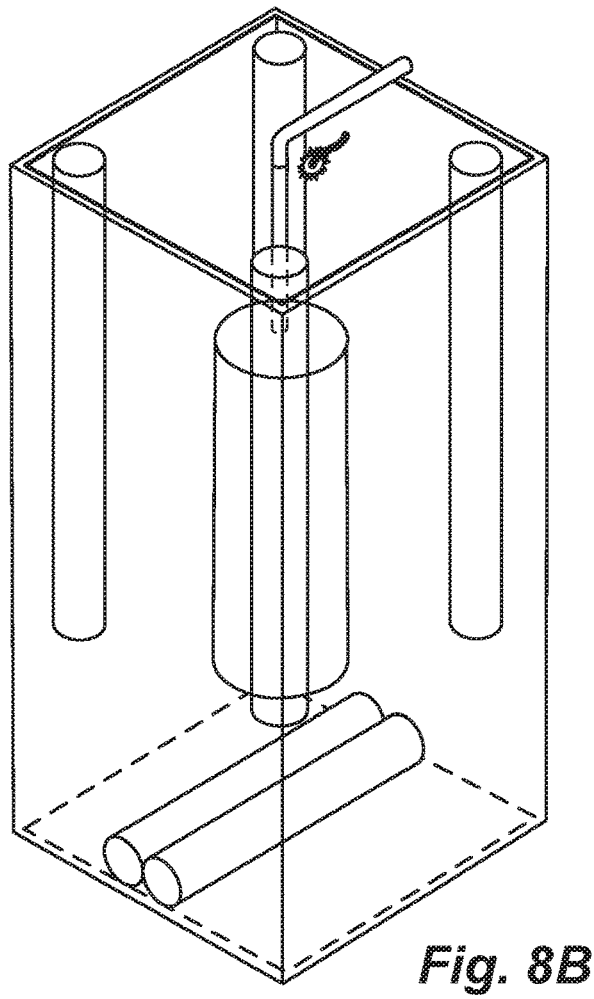
Figure 9A:
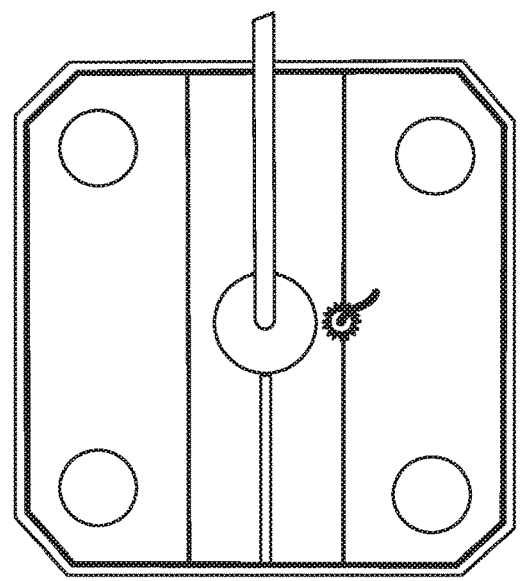
FIGS. 9A-9B are simplified views that show UV-C radiation sources and fiber optic UV-C radiation sensors within an octagonal parallelepiped disinfection device according to FIGS. 8A-8B.
Figure 9B:
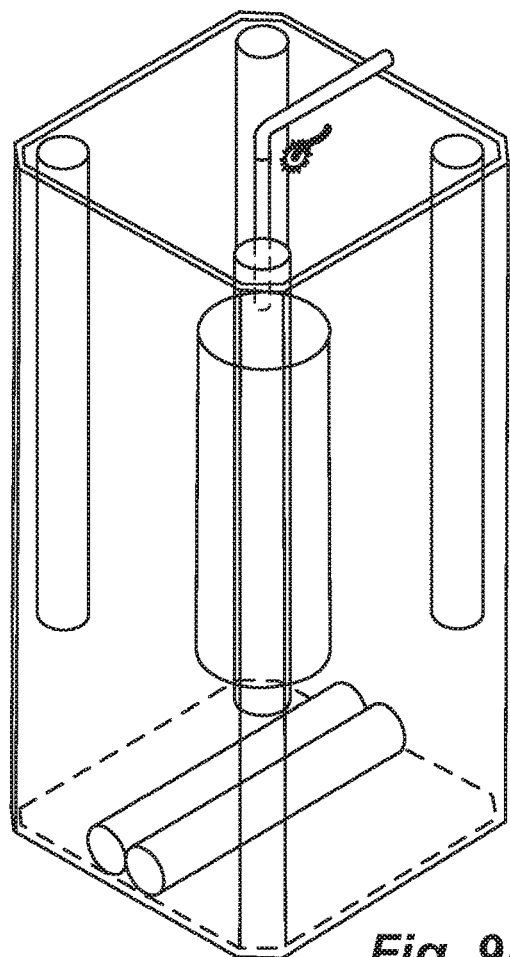
Figure 10A:
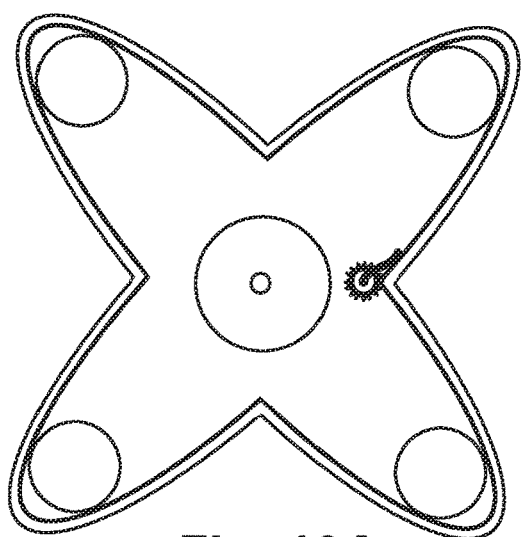
FIGS. 10A-10B are simplified views that show UV-C radiation sources and fiber optic UV-C radiation sensors within a double elliptical disinfection device according to another variation.
Figure 10B:
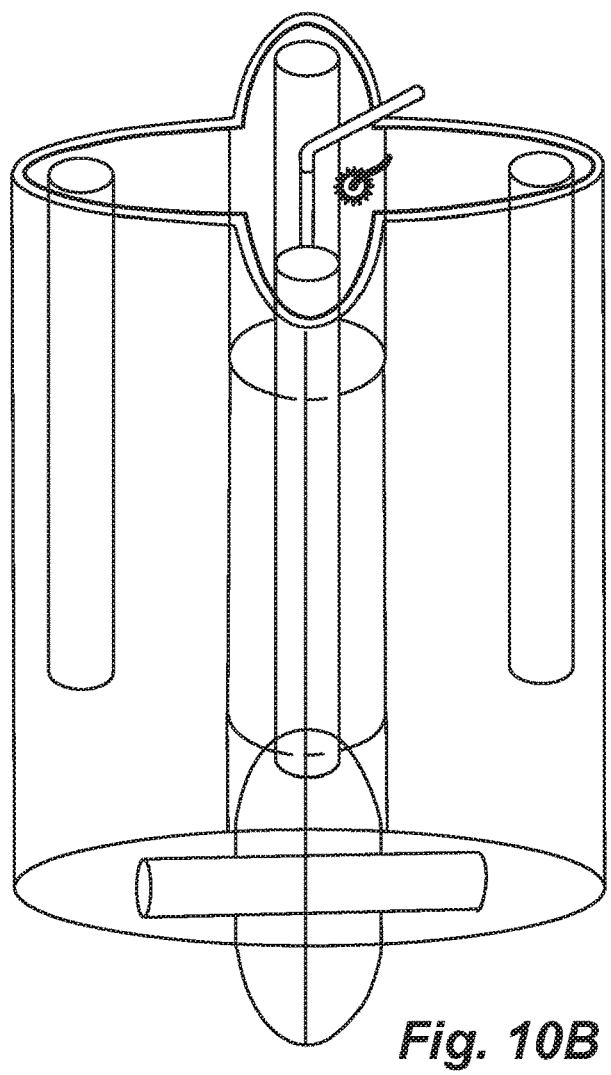

In other embodiments, e.g., when the interior volume of the disinfection chamber 400 has a cross-section shaped as an octagonal parallelepiped, as shown in FIGS. 4A-4B, the UV-C radiation sources 402 are configured so that one of four sources is positioned in each corner of the chamber encircling the target article, e.g., ultrasound probe 404, and two sources 402a are positioned on the bottom of the chamber under the probe 304. One or more radiation sensors 406 are positioned to measure radiation within the interior volume of the disinfection chamber 400. In cases where two or more radiation sensors 306 are included, the radiation sensors 306 may be cooperatively positioned to measure the radiation in different parts of the disinfection chamber 400. In some cases, multiple radiation sensors 306 are placed in close proximity to each other such that data collected from the plurality of radiation sensors may be compared to indicate that the collected data is valid and the disinfection chamber 400 is operating normally. Some octagonal parallelepiped variations may include only one source on the bottom of the chamber.

In addition to its physical configuration and the nature and number of disinfecting radiation sources provided within the disinfecting chamber, the dimensions of the interior volume formed by the disinfecting chamber and the positioning of the radiation sources within the disinfection chamber may be selected to create one or more disinfection regions. For example, the intensity of UV-C radiation emitted from a point source into space as a spherical field or from a line source into space as a cylindrical field, decreases as the inverse square of the distance from the source. To better ensure that high-intensity radiation is delivered to the articles to be disinfected, both on a so-called first pass from the source (i.e., the radiation emitted travels directly to, and strikes, the target; also called direct source radiation) and on subsequent reflection and/or re-radiation (i.e., indirect source radiation), the disinfection chamber can be configured to exhibit a substantially symmetric chamber, wherein the one or more articles to be disinfected can be positioned in a generally central location. Further the dimensions of the disinfection chamber can be selected to maintain the one or more sources of disinfecting radiation in close proximity to the one or more articles to be disinfected. For example, in certain embodiments, the disinfection chamber may be configured such that no dimension of the interior volume of the disinfection chamber exceeds 100 cm. In particular embodiments, no dimension of the interior volume defined by the disinfection chamber exceeds a length selected from 100 cm, 80 cm, 70 cm, 60 cm, 50 cm, 40 cm, 30 cm, and 20 cm or another like value. Where the disinfection chamber includes a disinfection region in the center of the chamber, and the one or more articles to be disinfected are positioned within the centered disinfection region during a disinfection process, in certain embodiments, the cross sectional dimensions of the width of the chamber do not exceed 40 cm in any dimension. In certain such embodiments, the cross-sectional dimensions of the width of the disinfection chamber may be selected from no larger than 30 cm in any dimension, no larger than 20 cm in any dimension, no larger than 15 cm in any dimension, and no larger than some other like distance in any dimension. In such embodiments, the length of the volume formed within the disinfection chamber can be selected to suit the one or more articles to be disinfected.

To facilitate positioning of contaminated articles within the disinfection device, the disinfection chamber can be provided with a suspension assembly that positions one or more articles, e.g., an ultrasound probe or other medical instrument, within the chamber. A suspension assembly as described herein works to position one or more articles to be disinfected consistently within the disinfection chamber. In these cases, where the disinfection chamber is designed to create one or more disinfection regions, providing a suspension assembly allows consistent, repeatable positioning of the one or more articles to be disinfected within disinfection region(s), thereby ensuring the one or more articles are subjected to high intensity radiation during a disinfection cycle.

In particular embodiments, a suspension assembly may be provided that positions a contaminated article in a central portion of the disinfection chamber, where a disinfection region of high-intensity radiation is created. In some variations, for instance, when the article is connected to a cable that may then extend out of the chamber, the suspension assembly comprises a slot at the top of the assembly that extends to a central portion of the top of the disinfection chamber. For example, as shown in FIG. 1, suspension assembly 114 includes a channel 116 having a proximal end 118 and a distal end 120. The proximal end 118 of channel 116 opens into access opening 112, and the distal end 120 of channel 116 is closed. As shown in the figure, distal end 120 terminates in an aperture 122 within which a cable of one or more articles (not shown) can be placed. Where provided, an aperture 122 will generally be provided to allow placement of the one or more articles within a disinfection region, such as at the center of the top 106 of the disinfection chamber 110 shown in FIG. 1. Although the aperture 122 shown in FIG. 1 is round, any suitably shaped aperture may be employed. In use, the cable portion of an article may be threaded through or otherwise introduced into channel 116 until it is disposed within the aperture 122 so that the active portion may be suspended within a central portion of the disinfection chamber 110. After the cable portion is introduced, a flap 124 may be actuated to close the channel 116.

In further variations, the article to be disinfected may be supported or suspended within the chamber by other coupling or attachment components. For example, where the article to be disinfected includes a cable, the cable portion may be removably coupled, attached, or secured to a portion of a wall of the disinfection chamber to support or aid in suspension of the article within the chamber. Alternatively, the article to be disinfected may be contained within the chamber with no portion extending without. In such an embodiment, the coupling or attachment components are contained within the chamber, and secure the article within a disinfection region. A suspension assembly included within the chamber or operating in conjunction with the disinfection chamber can include a pair of complementary mating elements, a hook or other device from which the article can be hung or suspended, a belt, or any other suitable feature, device, or mechanism for securely positioning an article to be disinfected within the disinfection chamber. Where the suspension assembly and the article are configured such that the suspension assembly comes in contact with a surface of the article, such as may occur, for example, with certain untethered articles that cannot be positioned via a tethered cable, the suspension assembly may be constructed of a material that is electromagnetically (e.g., optically) transparent to the disinfecting radiation (e.g., UV-C radiation). Such a configuration serves to avoid or reduce shielding of the article surface from UV-C radiation. Suitable materials for providing electromagnetically (e.g., optically) transparent suspension assemblies are known in the art (e.g., quartz glass (i.e., fused silica), poly-methyl-methacrylate (PMMA), clear polyethylene, and the like) and include, for example, known waveguide and lens materials which exhibit low energy absorption or low transmission loss of electromagnetic radiation.

In certain embodiments, where the disinfection chamber includes multiple sources of disinfecting radiation, the suspension assembly may be provided within the disinfection chamber such that an article to be disinfected is positioned within the disinfection chamber at a location that is equidistant from each source of disinfecting radiation. Such a configuration can facilitate homogeneous delivery of disinfecting radiation to each surface of the article. Alternatively, the suspension assembly and article to be disinfected can be designed so that the suspension assembly only contacts the article in an area that a medical practitioner can confirm is not contaminated or does not need to be disinfected. For instance, in the context of a medical device such as an endotracheal or ultrasound probe, the suspension assembly may be configured such that it does not contact any area of the article that comes in contact with a patient. In such embodiments, the intensity or uniformity of the radiation reaching the area of the article contacted by the suspension assembly may be of less importance.

The number and positioning of the one or more sensors included in the disinfection device are also selected to provide rapid, high-level disinfection at a low temperature. For purposes of the present description, a sensor (e.g., sensor 306 of FIG. 3 or sensor 406 of FIG. 4) includes any device or assembly of components that collects and measures an environmental condition. When referring to one or more sensors for detecting disinfecting radiation within the disinfection chamber, the one or more sensors will each be a device or assembly of components capable of collecting information regarding the disinfecting radiation present in the disinfection chamber, sensing or measuring the amount of disinfecting radiation within the disinfection chamber, and amplifying or processing the collected information regarding the disinfecting radiation. Further, in the context of the present description, a sensor is considered to be positioned within the disinfection chamber where any component of the sensor capable of detecting, measuring, transmitting, processing, or communicating processed information regarding the disinfecting radiation present within the disinfection chamber is positioned within or exposed to the interior of the disinfecting chamber.

Each of the one or more sensors included in the disinfection devices described herein may be capable of detecting and communicating information such as a total radiation dose, a rate of exposure over time, and the like. For example, where UV-C light is used as the disinfecting radiation, the sensors may sense the UV-C dose received by the target article and/or the amount of UV-C radiation emitted by one or more UV-C sources included in the disinfection device. In some embodiments, UV-C sensors included in the disinfection devices described herein may be one or more photodiodes positioned within the disinfecting chamber. In other embodiments, the one or more sensors may comprise one or more light conducting components such as fiber optic cables or light pipes that conduct the collected disinfecting energy to a detector, such as a photodiode. In some variations, the sensors within the disinfection chamber are configured to have a band-pass optical filter or other electromagnetic filter in front of them so that only radiation in the spectrum of interest is sensed. In some embodiments, one or more sensors may be positioned on or incorporated into the one or more articles to be disinfected. Positioning of one or more sensors on the one or more articles to be disinfected may provide a more accurate reading or assessment of the disinfecting radiation reaching the article. The devices described herein may include one or more sensors that utilize, for example, multiple optical conductors positioned to monitor direct and indirect sources of the disinfecting radiation. Photonic conductors useful in the context of the devices described herein include, but are not limited to, fiber optic "cable" (suitable for conducting light over longer distances with low loss) or a simple "light pipe" formed of a glass, polymer, or other simple, optically transmissive material that traps and contains light within itself and conducts the light with low loss. Where used, a "light pipe" as referenced herein is typically more suited to conducting light over relatively short distances.

The multiple fiber optic conductors may lead back to a single detector or the conductors may lead back to multiple detectors, delivering their radiation signal to a single or multiple photodiodes. For example, in such an embodiment, each one of a first set of one or more fiber optic cables may be used to directly monitor each of the disinfecting radiation sources (e.g., each source is paired with a fiber optic cable), and a second set of one or more fiber optic cables may be positioned to monitor the aggregate disinfecting radiation from direct and indirect sources present in the disinfection chamber. In still other embodiments, a third set of one or more fiber optic cables may be used for collecting and monitoring disinfecting radiation within the disinfection chamber from indirect sources of disinfecting radiation. In one such embodiment, one or more of a third set of fiber optic cables may be positioned to face one or more of the sidewalls of the disinfecting chamber to primarily monitor a reflected quantity of disinfecting radiation. It is to be understood that the first, second, and third sets of one or more fiber optic cables are labeled such for convenience of description only. A device according to the present description may include one or more sensors that utilize any one of or any combination of two or more of the first, second, and third sets of fiber optic cables described here. However, configuring one or more sensors to include multiple fiber optic cables positioned to monitor direct, aggregate, and/or indirect disinfecting radiation may be advantageous. For example, using such a configuration, one may assess the condition of each of the direct sources of disinfecting radiation, monitor the input radiation levels to ensure the direct sources of disinfecting radiation are working, and, in some cases, drive the source system in a closed loop fashion to achieve and maintain a selectable and in addition or in the alternative a selected radiation power level (i.e., irradiance) and resultant radiated dose.

"Shadowing" of the one or more sensors included in the disinfection device is likely to occur when one or more articles to be disinfected are positioned for treatment within the disinfection chamber. The effect termed "shadowing", as used herein, has two primary meanings; one which refers to a possible drop in total UV-C radiation detected or "seen" by one or more sensors due to the presence of an article to be disinfected, and second the situation where some portion of the article blocks and prevents some amount of radiation from reaching another part of the article, or other articles if more than one is present in the chamber. The shadowing might be direct (i.e., the article is positioned between the UV-C source and the detector), virtual (i.e., the article absorbs UV-C radiation and/or prevents reflection of UV-C radiation that might otherwise be detected by one or more sensors), or a combination of direct and virtual. In order to reduce or avoid the potential impact of shadowing, and to increase the system's tolerance (i.e., reduce sensitivity to shadows) for probes or articles of different sizes and shapes, one or more UV-C sensors may be positioned at preferred locations such as the upper or lower regions of the disinfection chamber if the one or more articles to be disinfected are positioned in a central area within the chamber. Further, shadowing caused by different sizes or shaped articles positioned within the disinfection chamber can be assessed and disinfection control conditions can be adjusted based on the extent to which shadowing is present. For example, where a shadowing effect is present, the dose of UV radiation received by a detector or detectors over a given exposure time is reduced since less radiation is able to reach it, compared to the dose that would be received in the same time absent a shadowing effect. Further, if multiple articles are included within a disinfection chamber, shadowing of one or more articles may be caused by the presence of the one or more additional articles. Even further, the disinfection system may detect the presence of one or more articles within the disinfection chamber via the drop in radiation signal due to shadowing.

In cases where one or more sensors experience shadowing due to the presence of one or more articles to be disinfected even though there is no shadowing of the one or more articles themselves, the disinfection system may include a system control algorithm that operates to maintain a targeted disinfection time despite the lower level of disinfecting radiation detected by the one or more sensors. In alternative embodiments, where shadowing of a disinfection radiation sensor occurs, a system control algorithm may be configured to take into account the shadowing effect and adjust (e.g., increase or decrease) the process time for a disinfection cycle. For example, where a sensor is shadowed, but the one or more articles being disinfected are not, the sensor will receive and communicate a level of irradiance and thus disinfecting radiation that is lower than the actual amount being delivered to the disinfection chamber. In such an embodiment, a system control algorithm may be configured to take into account the shadowing effect and adjust the cycle times such that the total dose of disinfecting radiation does not exceed a selected threshold dose. Proper placement of the one or more sensors, sources, and reflective surfaces, together with the location of the article in the disinfection region, reduce or eliminate sensor shadowing effects and hence reduce the opportunity for mis-measurement and misinterpretation of radiation levels in the chamber.

The positioning and/or configuration of the one or more sensors within the disinfection chamber will generally be selected to provide rapid, high-level disinfection at a low temperature. For example, the sources of UV-C radiation may be positioned within the disinfection chamber to provide an acceptably uniform spatial distribution of UV-C radiation throughout the chamber, and the one or more UV-C sensors included within the disinfection chamber may be positioned to detect the aggregate dose of UV-C radiation delivered within the chamber and positioned to monitor that distribution of the UV-C radiation within the chamber is suitably uniform. In specific embodiments, the one or more sensors in the disinfection chamber may be positioned to sense the overall contribution of UV-C radiation emitted from all sources (direct and indirect contribution). "Direct" sources of emitted UV-C radiation include the UV radiation sources themselves, and "indirect" sources of emitted UV-C radiation are features (e.g., chamber walls, the article being disinfected, etc.) that are not themselves sources of UV-C radiation but which reflect and/or re-radiate incident UV-C radiation received from the direct and other indirect sources. One sensor or a plurality of sensors may be used to obtain irradiance values to be further processed. The signals obtained from the other sensors may be treated or filtered independently, be compared to different predetermined target doses, may have distinct circuitry, and be processed separately and according to different algorithms.

It may be beneficial in some embodiments to include one sensor or a set of sensors to detect the global radiation dosage delivered to the chamber and another sensor or set of sensors to check or monitor each source directly and without any potential for experiencing a shadowing effect due to the presence of an article to be disinfected. In such an embodiment, a disinfection cycle executed by the device could be triggered to stop after sufficient time for 1) a threshold aggregate dose of UV-C radiation to be received within the disinfection chamber (e.g., when the average UV-C exposure, measured by summing the signal across each of a selected one or more sensors included within the disinfection chamber, reaches a specified value) with one or more sensors placed so that shadowing does not impact the UV-C exposure received by any one sensor by more than 30% and 2) one or more of the individual sensors to receive a dose of UV-C radiation that meets or exceeds a defined threshold. The thresholds for UV-C dosing are set to achieve high-level disinfection, and the threshold can be determined for a given article and targeted pathogen(s) using, for example, methods described herein. In particular embodiments, the disinfection chamber is configured and the UV-C sources and sensors are positioned such that shadowing does not impact the UV-C exposure received by any one sensor by more than an amount selected from 25%, 20%, 15%, 10%, and 5% or a like value.

In one embodiment, a disinfection system as described herein is controlled to run a disinfection cycle for a period of time selected to result in a predetermined dose of disinfecting radiation being delivered into a disinfection chamber. In such an embodiment, the system is controlled such that, once the disinfection cycle has run for the selected time, the information regarding a disinfecting radiation dose collected from the sensors is checked, and the cycle is stopped if one or more sensors have received a predetermined threshold (e.g., minimum) dose. For example, where UV-C radiation is used as the disinfecting radiation, in particular embodiments, the predetermined threshold dose may be selected from between about 50,000 $\mu J/cm^2$ and about 10,000,000 $\mu J/cm^2$. In certain such embodiments, the dose may be selected from between about 50,000 $\mu J/cm^2$ and about 1,000,000 $\mu J/cm^2$, such as, for example, a dose selected from between about 50,000 $\mu J/cm^2$ and about 750,000 $\mu J/cm^2$, between about 50,000 $\mu J/cm^2$ and about 650,000 $\mu J/cm^2$, between about 50,000 $\mu J/cm^2$ and about 500,000 $\mu J/cm^2$, between about 50,000 $\mu J/cm^2$ and about 450,000 $\mu J/cm^2$, between about 50,000 $\mu J/cm^2$ and about 350,000 $\mu J/cm^2$, between about 50,000 $\mu J/cm^2$ and about 250,000 $\mu J/cm^2$, and between about 50,000 $\mu J/cm^2$ and about 100,000 $\mu J/cm^2$ or between other like values. In further such embodiments, the dose may be selected from between about 150,000 $\mu J/cm^2$ and about 750,000 $\mu J/cm^2$, between about 150,000 $\mu J/cm^2$ and about 650,000 $\mu J/cm^2$, between about 150,000 $\mu J/cm^2$ and about 500,000 $\mu J/cm^2$, between about 150,000 $\mu J/cm^2$ and about 450,000 $\mu J/cm^2$, between about 150,000 $\mu J/cm^2$ and about 350,000 $\mu J/cm^2$, and between about 150,000 $\mu J/cm^2$ and about 250,000 $\mu J/cm^2$ or between other like values. In still further such embodiments, the dose may be selected from between about 250,000 $\mu J/cm^2$ and about 750,000 $\mu J/cm^2$, between about 250,000 $\mu J/cm^2$ and about 650,000 $\mu J/cm^2$, between about 250,000 $\mu J/cm^2$ and about 500,000 $\mu J/cm^2$, between about 250,000 $\mu J/cm^2$ and about 450,000 $\mu J/cm^2$, and between about 250,000 $\mu J/cm^2$ and about 350,000 $\mu J/cm^2$ or between other like values.

If the selected threshold dose has not yet been achieved, the disinfection system may continue to run for an interval of time set to bring the total exposure to the disinfecting radiation up to the selected (e.g., minimum) threshold. In such an embodiment, the selected threshold of disinfecting radiation can be determined in one of many different ways. For example, the system can be configured and controlled to stop a disinfection cycle once it is confirmed that one or more of the following conditions have been satisfied: 1) each of the sensors have received a predetermined (minimum) dose of disinfecting radiation; 2) the average dose received by the sensors has reached a threshold (e.g., minimum) dose; 3) at least one individual sensor has received a first threshold (e.g., minimum) dose and all the remaining sensors have received a second threshold (e.g., minimum) average dose; 4) one or more sensors positioned to directly receive disinfecting radiation have received a first threshold (e.g., minimum) dose and one or more additional sensors positioned to monitor aggregate or indirect radiation have received a second threshold (e.g., minimum) dose; and 5) a first group of two or more sensors have received an average dose that meets a first threshold (e.g., minimum) dose and a second group of two or more additional sensors have received an average dose that meets a second threshold (e.g., minimum) dose. As used herein, the terms "first threshold dose" and "second threshold dose" do not necessarily refer to different values. The first and second threshold doses of disinfecting radiation may be the same, or, in other embodiments, the first and second threshold doses may be different.

In addition to one or more sensors capable of detecting or quantifying the disinfecting energy delivered within the disinfection chamber and to the article to be disinfected, the disinfection chamber may also include one or more temperature sensors. In particular embodiments, disinfection processes, according to the present description, take place at acceptably low temperatures. In one embodiment, where the surface temperature of the article being disinfected is to be maintained below a particular threshold, one or more temperature sensors, such as one or more infrared temperature sensors may be used to monitor and report the surface temperature of the article being disinfected. Alternatively, it may be sufficient to simply monitor the air temperature within the chamber or the temperature of one or more of the disinfection chamber walls. Where the air temperature or a wall temperature within the disinfection chamber is monitored, the monitoring location may be selected to best detect or determine the surface temperature of the one or more articles being disinfected to a reasonable accuracy. In such embodiments, a location for temperature monitoring within the disinfection chamber that correlates to the surface temperature of the one or more articles being disinfected can be selected via testing that monitors the surface temperature of the articles and identifies an area or location within the chamber that exhibits a temperature that is suitably correlated to the article surface temperature. In such an instance, the disinfection chamber may include one or more ambient temperature sensors that monitor and communicate the ambient temperature of the disinfection chamber while a disinfection cycle is being carried out.

A temperature control system may also be included in the devices and systems described herein. In such embodiments, the temperature control system may work to cool the disinfection chamber and may include, for example, one or more components that provide cooling such as passive heat sinks and fins, ventilating air moving fans, liquid-based heat exchanger/radiator components, thermo-electronic Peltier type devices, refrigeration cycle systems, and the like. In other embodiments, the temperature control system may be configured to maintain the disinfection chamber within a selected temperature range during the entirety of each disinfection cycle. For instance, it has been found that light tubes generating UV-C radiation work with an acceptable efficiency at a tube surface temperature of between about 35° C. and about 45° C. In certain embodiments, a temperature control system as described herein may be configured to: 1) warm the disinfection chamber to a temperature within a selected or selectable temperature range for the one or more sources of disinfecting radiation prior to initiation of a disinfection cycle; and 2) maintain the disinfection chamber within a temperature range that does not result in undesired degradation of the articles being processed but also does not move below the selected threshold temperature range for the source(s) of disinfecting radiation. In order to maintain the disinfection chamber at an acceptable temperature, the temperature control system may include one or more sources of heat. In such embodiments, the sources of heat may include the one or more radiation sources (e.g., one or more UV-C tubes) or any other suitable source of heat or heating element, including known electrical heating devices (e.g., resistive, eddy-current, etc.), infra-red heating devices, and radiant (e.g., infrared (IR)) heating devices.

Where the disinfection chamber includes walls formed of or coated with a material that preferentially absorb longer wavelengths of radiation (e.g., IR radiation), the walls themselves may accumulate heat energy, and heat from the walls may be re-radiated into the disinfection chamber. In order to manage heat within the chamber, the disinfection device may include one or more heat sink elements in thermal association with the disinfection chamber walls. For example, a heat exchanger or cooling element might be positioned against the outside surface of the walls forming the disinfection chamber. Alternatively, a heat exchanger or cooling element may be disposed within the walls of the disinfection chamber between the inside and outside surfaces. In either configuration, standard heat exchange or cooling systems may be used, and in both configurations, as the wall(s) are heated through absorption of particular wavelengths of radiation, the heat exchanger or cooling system removes or otherwise transfers heat from the wall(s) and works to maintain an acceptably low temperature within the disinfection chamber.

The devices and systems described herein may or may not be portable. Devices and systems according to the present description can be configured to suit the chosen parameters of the particular context and application in which the devices and systems will be put to use. In embodiments where the housing is portable, the housing may be moved in close proximity to the article, or a portion of the article, that requires high level disinfection. In certain contexts, portability of the devices and systems according to the present description is advantageous; as such portability reduces or eliminates the need to bring the articles to be disinfected to the device or system itself. When the embodiment is portable, the devices and systems may be configured to utilize any power source commonly located within a home, clinic, or hospital setting. Alternatively, in embodiments of a portable device or system as described herein, one or more components of the system may be powered by one or more batteries or other portable power sources to reduce or eliminate the need to access a fixed power source. Various batteries, battery technologies, and power management technologies are well-known in the art and can be utilized in devices and systems according to the present description.

The disinfection devices described herein may also include a component that records traceability information of disinfection and/or a component that indicates to the user the condition of the article (e.g., an ultrasound probe) after the article has been subjected to a disinfection cycle (e.g., a green light or light source of another color can be activated when the chosen requirements have been fulfilled such as a required/minimum dose reached, temperature maintained within boundaries, etc., and a red light or light source of another color can be activated if the chosen requirements have not been satisfied). In other variations, the device has a component that records and signifies traceability information about the latest use or one or more other previous uses. Here the traceability information will indicate whether the latest event was a disinfection procedure or another use (e.g., a green light or light source of another color could be activated if the latest use was a successful disinfection, and a red light or light source of another color activated if not). In addition, or in the alternative, another type of output device such as a printer may be used to produce a physical record of the disinfection just completed. The traceability and indicator component may be a tag, a collar, or some other device, which further may comprise one or more of the photodiode(s) detectors, which further can be affixed to the article being disinfected or other related component (e.g. a cable or tether, if one exists). The tag or collar device may include identification data and thus also serve as an identification component. The tag or collar may also be configured to hang or otherwise assist in positioning the article in the disinfection chamber.

Disinfection systems as described herein include a device according to the present description controllably linked to one or more processors. A processor utilized in the disinfection systems described may include or execute software to provide system control, monitoring, or other functions such as by running or using one or more algorithms operable for system monitoring and control based on one or more predetermined system or process parameters. Systems according to the present description may utilize one or more algorithms operable to accomplish one or more of managing the disinfection cycle of the disinfection device, calibrating, monitoring the disinfection conditions, adjusting the disinfection conditions, monitoring status and condition of one or more system components, defining disinfection conditions, initiating disinfection processes, terminating disinfection processes, and adjusting system operation or disinfection conditions based on historic system data, real-time system data, or other like data.

In one embodiment, for example, the algorithm may operate to terminate a disinfection cycle when predefined conditions are reached and system parameters such as temperature, shadowing, and system component operating conditions have been taken into account. In such an embodiment, the predefined dose requirement may be a defined combination of average and specific doses of UV-C radiation detected by the sensors positioned within the disinfection chamber. The processor may also operate to terminate the disinfection cycle after a predetermined amount time has elapsed and it has been confirmed that a selected dose of disinfecting radiation has been delivered to the disinfection chamber. For example, the processor may operate to terminate the disinfection cycle after 600 seconds, 540 seconds, 480 seconds, 420 seconds, 360 seconds, 300 seconds, 240 seconds, 180 seconds, 120 seconds, 100 seconds, 90 seconds, 60 seconds, 45 seconds, 30 seconds, 15 seconds, and 10 seconds, or another like number. Some processors may be configured to run combinations of algorithms that terminate a disinfection cycle once a predetermined cycle time has elapsed, an average dose of UV-C radiation measured from the one or more of UV-C sensors reaches a predetermined UV-C dose requirement, and a predetermined UV-C dose threshold is reached at one or more of the individual UV-C sensors.

Figure 11A:
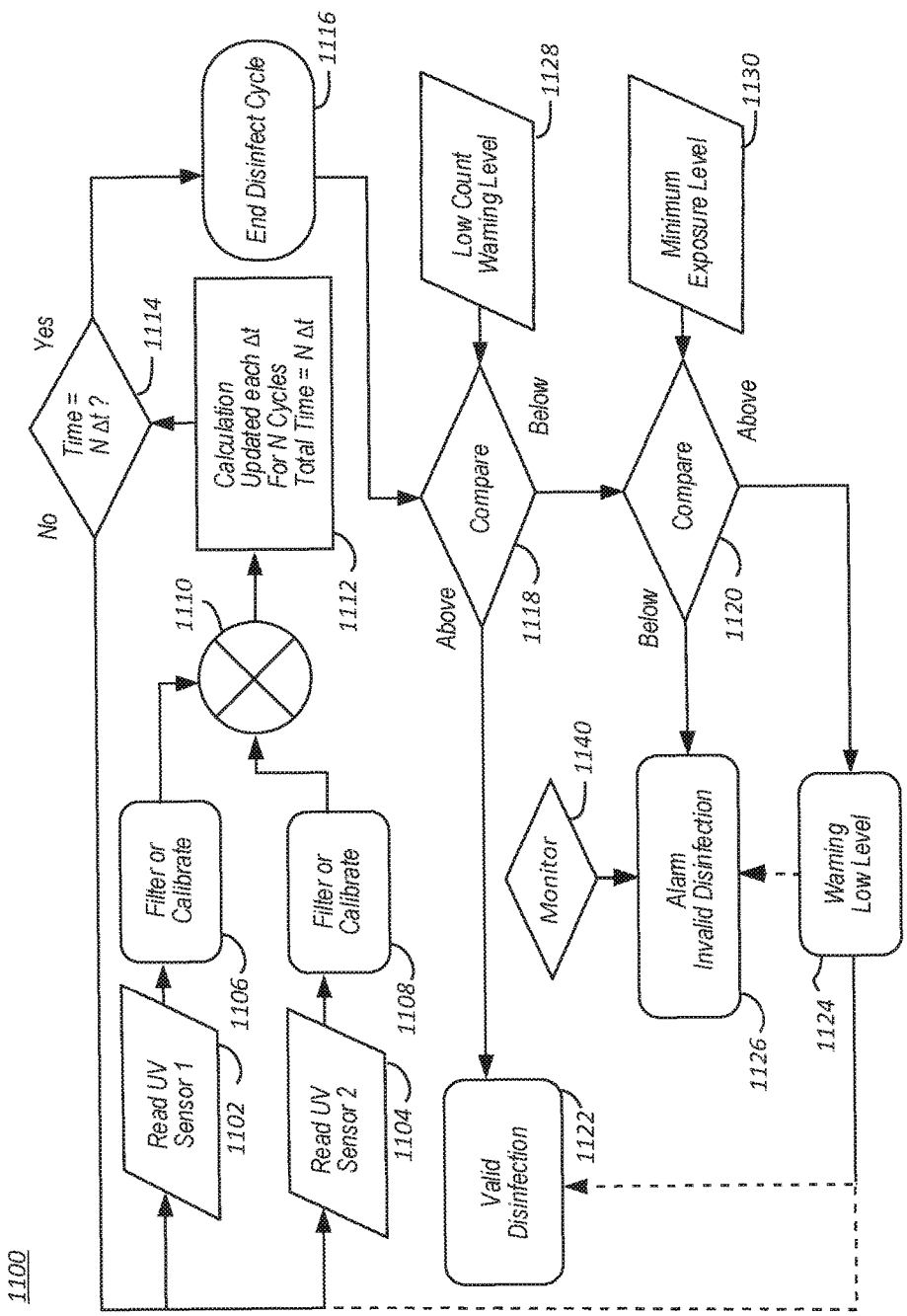
FIGS. 11A-11B illustrate an exemplary disinfection cycle and exemplary system monitoring and control algorithms running in parallel.
Figure 11B:
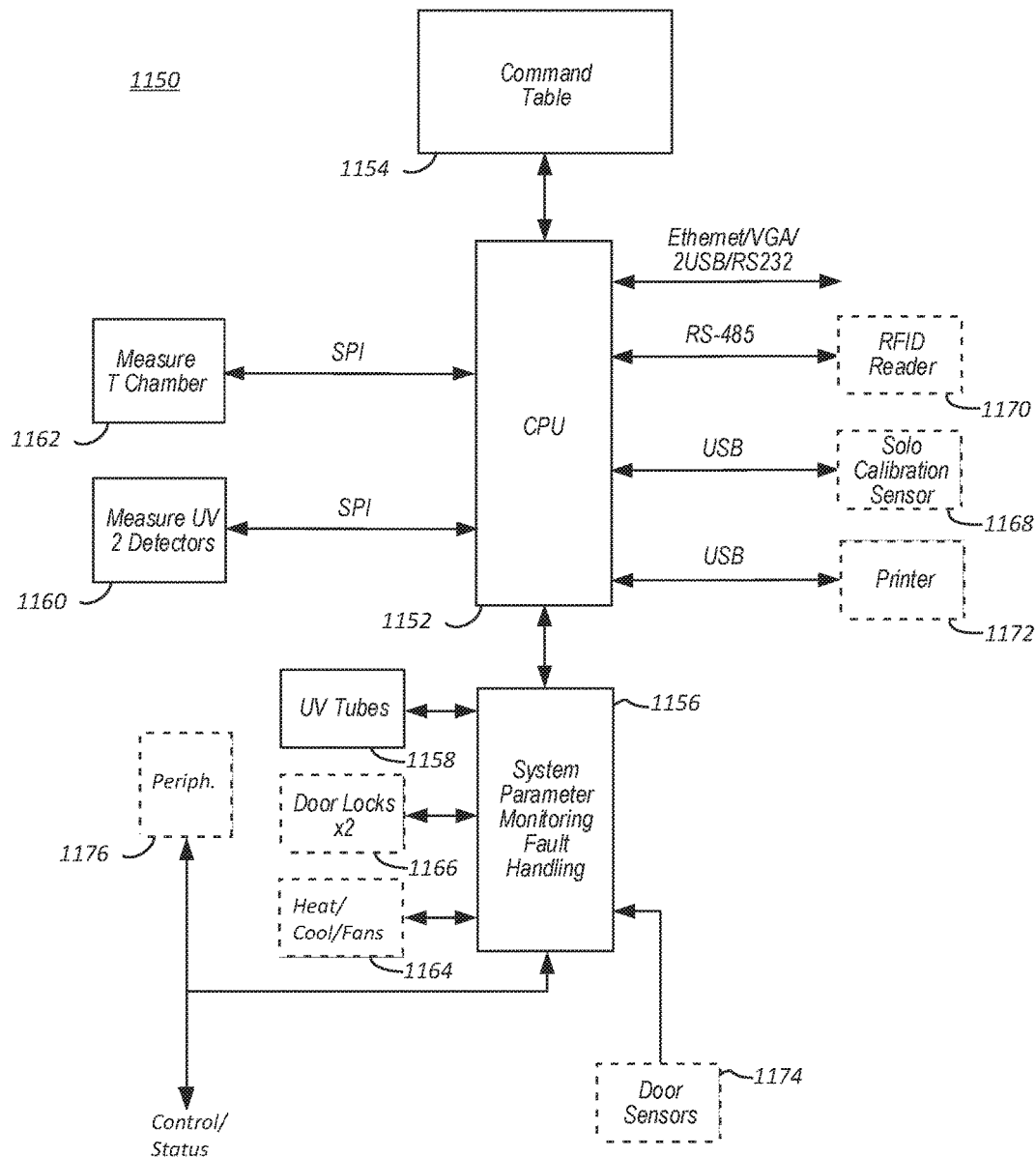

In addition to managing a disinfection cycle, the one or more processors may further run or use an algorithm that monitors and controls the operating state of the disinfection device and system parameters to determine whether the device performs as directed. Exemplary system parameters include, but are not limited to, lamp driving current and/or voltage, operating temperature range(s), status and operation of temperature sensors, status and operation of a temperature control system, presence of one or more articles to be disinfected, identity and provenance of said article, and status of chamber door and other interlocks. The disinfection cycle and system monitoring algorithms may or may not be run in parallel. A disinfection device may run a disinfection cycle monitoring and control algorithm and a system monitoring and control algorithm in parallel as illustrated in FIGS. 11A and 11B. In particular embodiments, the system includes a system control algorithm, which may be run on the one or more processors included in the system. In such embodiments, the system receives information from a variety of sources, and may operate to provide an independent check on a primary approach to monitoring and control of a disinfection cycle.

FIG. 11A is a flowchart 1100 illustrating processes that may be used by embodiments of an exemplary monitoring and control system 1150 (FIG. 11B) for high level disinfection procedures. In this regard, each described process of the flowchart may represent a module, segment, or portion of software code, which comprises one or more executable instructions for implementing the specified logical function(s). It should also be noted that in some implementations, the functions of the associated process may occur in a different order, may include additional functions, may occur concurrently, and/or may be omitted.

Referring to FIG. 11A, a disinfection cycle monitoring and control algorithm 1100 may first take readings 1102, 1104 from one or more sensors, e.g., sensors 1 and 2, by known techniques. The techniques may include retrieving radiation measurement values from one or more photodiodes of sensor 1 and sensor 2. Sensor 1 and sensor 2 may each include one or more photodiodes. For purpose of explanation, the photodiodes of sensor 1 may be measurement photodiodes and the photodiodes of sensor 2 may be reference photodiodes. Thus, readings taken at 1102 includes the act of retrieving values representing the amount of radiation received by one or more measurement photodiodes, and readings taken at 1104 includes the act of retrieving values representing the amount of radiation received by one or more reference photodiodes.

The measurement photodiodes of sensor 1 are arranged within a disinfection chamber and configured to collect the amount of radiation received by articles to be disinfected. The articles to be disinfected may be a plurality of articles to be disinfected. Accordingly, one photodiode may be arranged to collect the radiation received by one portion of one article, by one portion of multiple articles, by one article, by several articles, or by some other like aspect.

The reference photodiodes of sensor 2 are arranged in proximity to one or more radiation sources. In a calibration procedure, radiation source can be activated and values can be collected by sensor 2 and recorded. In some cases, the calibration procedure includes reading sensor 2 as one or more parameters associated with the radiation source are varied and recording the values collected by sensor 2 under the varying conditions. In some cases, readings from sensor 1 are also taken and recorded. In this way, radiation values from sensor 2 may be associated with particular conditions of a radiation source, and in addition or in the alternative, radiation values from sensor 2 may be associated with radiation values of sensor 1. If the calibration procedure records values from one or more sensors under controlled test conditions, the association between the readings can be used when articles are placed and irradiated in the disinfection chamber during normal use conditions.

The calibration procedure is employed to account for variations in the output of a radiation source. Many factors can contribute to the variations in output. The factors may include temperature, time in service, input power, physical state of the source based on past use or abuse of the chamber, and many other factors. Accordingly, a calibration procedure can measure actual output of a radiation source during controlled conditions, and the values collected during the calibration procedure can be applied to adjust sensor values collected during normal conditions. For example, a calibration procedure may capture a certain value "X" from sensor 2 when a radiation source is enabled with a known set of parameters. Later, during normal use of disinfection with the same parameters applied to the radiation source, a value of 75% of X may be captured at sensor 2. Based on the captured value, it may be appropriate to scale values collected at sensor 1 by 75% because it is recognized that 25% of the radiation did not reach the sensor.

The signals (i.e., values) read from sensors 1 and 2 may be conditioned at 1106, 1108 (e.g., subjected to calibration factors, filtered, or processed by some calculation or algorithm, etc.). As described herein, a calibration procedure may be executed to record parameters and collected values from the disinfection system under various conditions. The calibration procedure may be executed during all or part of a disinfection cycle, before or after a test procedure, as part of a periodic self-test, or at some other time. The parameters may include raising or lowering the temperature in the disinfection chamber, repositioning sensors in the disinfection chamber, enabling the radiation source for certain periods of time, certain power conditions, and at certain rates or periods. The calibration procedure may be used to generate scaling factors, weighting factors, normalization factors, calibration factors, mathematical correction factors, or the like. Subsequently, values reported by the sensors can be modified using such factors.

In some embodiments, the photodiodes of sensor 1 and sensor 2 output an analog value such as an electrical voltage or current representing an instantaneous amount of sensed radiation. The analog value may be applied to analog-to-digital circuitry, which will generate a digital count value within a known range; the count value representing the instantaneous amount of sensed radiation. In other cases, the photodiodes of sensor 1 and sensor 2 output a digital count value directly. The count value may represent an instantaneous or accumulated amount of sensed radiation. In some cases, the count value may be formed in a 10-bit binary number. The count value may thus take on any value between 0 and 1023. In such a case where the count value is a 10-bit number, a value of 0 will represent no radiation received by the one or more photodiodes of the sensor, and a value of 1023 will represent complete saturation of the photodiode with radiation. A count value in between 0 and 1023 will proportionally represent how much radiation was received by the one or more photodiodes of the sensor. The count values read at 1102 and 1104 may be modified by the application of a mathematical formula along with one or more values from the calibration procedure to create filtered, normalized, or otherwise calibrated count values at 1106 and 1108 respectively.

Next, the disinfection cycle starts at 1110 and proceeds for a timed interval to provide a defined dose of disinfecting radiation to the one or more articles being processed. The timed interval is also referred to herein as a "primary timed interval." The primary timed interval may be selected from a period of 600 seconds, 540 seconds, 480 seconds, 420 seconds, 360 seconds, 300 seconds, 240 seconds, 180 seconds, 120 seconds, 100 seconds, 90 seconds, 60 seconds, 45 seconds, 30 seconds, 15 seconds, 10 seconds, or some other like time value. In some instances the primary timed interval may be longer than 600 seconds or shorter than 10 seconds.

In some embodiments, during or at the end of the fixed time period, the detected radiation from the sensors is processed 1112. The processing may include an integration process, which accumulates sensor data over time to determine a total radiation dose from one or more sensors and, in certain embodiments, averaged over two or more sensors. In addition, or in the alternative, the processing may also include signal conditioning. The signal conditioning may include the linear application of correction factors generated during a calibration procedure. Alternatively, the signal conditioning may include more complex filtering algorithms, prediction algorithms, statistical analysis algorithms, and the like to generate more accurate indications of radiation applied to articles in the disinfection chamber.

When processing of the detected radiation signals occurs during the disinfection cycle, such processing can be programmed to take place at predetermined time intervals until the end of the fixed time period. In FIG. 11A, for example, in cooperation with the calculation acts of 1112, a predetermined time interval can be processed at 1114. If a predetermined time interval has elapsed, but the entire fixed time period (i.e., the primary timed interval) for the disinfection cycle has not elapsed, then processing from 1114 returns to read new data from sensor 1 and sensor 2 at 1102, 1104. Alternatively, if the entire fixed time period has elapsed, then program flow passes to the end of disinfection cycle processing at 1116 where one or more resulting values from the calculation stage 1112 are analyzed. The resulting one or more calculated values at the end of the fixed time period (i.e., primary timed interval) are compared to one or more threshold levels at 1118 and 1120. In a first case, if the one or more calculated values indicate that a sufficient dose of radiation has been administered, then processing at 1118 will advance to the end of a valid disinfection cycle 1122. Processing for the end of a valid disinfection cycle 1122 may include generating a visual, audio, tactile, or some other indication of success. Alternatively, processing from 1118 may advance to 1120 when the one or more calculated values indicate that a sufficient dose of radiation has not been administered. In these cases, it may be determined that an insufficient dose of radiation has been provided, but the insufficient dose is nevertheless above a second threshold. If the one or more calculated values are above the second threshold, processing may be passed to 1124 where a low warning level indicator is asserted and a decision is made regarding how to advance processing. In one case, if the administered dose of radiation is very low or for other reasons, the processing at 1124 may direct the system to extend the cycle (e.g., add time to the cycle to reach a valid state) and pass processing back to read data from sensors 1 at 1102 and sensor 2 at 1104. In another embodiment, the processing at 1124 may report the low level exposure warning at 1124 and nevertheless terminate the processing with an indication of valid disinfection at 1122. The case where a low-level warning is reported concurrent with an indication of valid disinfection may be used when an acceptable dose of radiation has been measured, but other circumstances have been noted such as extended disinfection time, elevated temperatures, doses of radiation that surpass a first, lower threshold but not a second, more desirable threshold. In still other cases, processing at 1124 may determine that the dose of radiation was above the second threshold at 1120, but other conditions of the disinfection chamber direct an indication of invalid disinfection at 1126. In such cases, the invalid disinfection may be caused by exceeding a number of times that extra radiation was delivered or other errors were recorded.

Returning back to the processing at 1120, if the one or more calculated values indicate that the insufficient dose of administered radiation is below the second threshold, then processing passes to 1126 where the cycle is terminated with an error condition.

The processing of the disinfection cycle monitoring and control algorithm 1100 may optionally include one or more user configurable parameters. For example, the fixed time period (i.e., primary timed interval) may be selectively configured, the predetermined time interval may be selectively configured, and other parameters may be selectively configured. At 1128, a first threshold, which is indicated as a low count warning level, may be selectively configured. At 1130, a second threshold, which is indicated as a minimum exposure level may be selectively configured. The first and second threshold values, which are described herein, are applied in the processes at 1118 and 1120, respectively.

The processing at 1102-1130 may be considered a disinfection algorithm. The disinfection algorithm may be formed of one or more software programs, subroutines, modules, or the like. The disinfection algorithm may be executed within an operating environment controlled by an operating system. Alternatively, there disinfection algorithm may also operate in an embedded controller environment that does not have an operating system.

A second algorithm to monitor the system parameters may also be executed within the system monitoring and control algorithm 1100. The monitor algorithm at 1140 may operate in parallel with the disinfection algorithm at 1102-1130. Alternatively, the monitor algorithm at 1140 may operate serially (i.e., in series) with the disinfection algorithm at 1102-1130, superior in priority to the disinfection algorithm at 1102-1130, subservient in priority to the disinfection algorithm at 1102-1130, or in some other cooperation with the disinfection algorithm at 1102-1130. Generally speaking, the monitor algorithm at 1140 will operate continuously when the disinfection device is in use.

The monitor algorithm at 1140 interacts with various logic modules of the disinfection device. In some case, the monitor algorithm at 1140 monitors operational state of various logic modules. In other cases, the monitor algorithm at 1140 interacts with a user or another computing program to interrogate current parameters, modify parameters, add parameters, delete parameters, and edit parameters. The various logic modules include parameters and status values associated with radiation source power (i.e., current, voltage, and the like), door locks, temperature sensors, cooling fans, electronic identification modules (e.g., RFID tags associated with an article being disinfected), and the like. The parameters and status values associated with the radiation source may be used in cooperation with a calibration process or calibration parameters (e.g., correction factors, scaling factors, and the like). The temperature sensor may be monitored to keep the disinfection chamber from exceeding one or more threshold temperatures, such as a preferable temperature below 35° C. and an acceptable temperature below 55° C. Door lock sensors may be monitored to reduce the chance that humans are exposed to the radiation energy produced by the radiation source. Cooling fan operation may also be monitored to control the temperature in the disinfection chamber. In some cases, active cooling may be employed to maintain the temperature in the disinfection chamber below one or more threshold temperatures for integrity of the articles being disinfected, for efficiency of the radiation source, or for other reasons. One or more identification modules can be monitored or controlled by the monitor algorithm at 1140. The identification module can read, for example, an RFID tag to determine which if any article is present in the disinfection chamber, which disinfection device is in use, the identity of the radiation source, and many other parameters to control data, track data, or the like.

The monitor algorithm at 1140 is configured to detect improper function or unsafe conditions of the disinfection device or articles within. In some cases, the monitor algorithm at 1140 operates continuously. Execution of the monitor algorithm at 1140 is generally independent from execution of the disinfection algorithm at 1102-1130, but as illustrated in FIG. 11A, certain conditions permit the monitor algorithm at 1140 to affect processing of the disinfection algorithm at 1126. In such cases, if an upper temperature threshold is exceeded, for example, the operation of the disinfection algorithm can be directed to shut down the radiation source, report an invalid disinfection, and direct other actions.

Various approaches may be taken to monitor and take disinfection cycle control action based on the radiation (e.g., UV-C) dose emitted by one or more radiation (e.g., UV-C) sources included in the disinfection chamber. In the embodiments discussed herein, the radiation source is referred to as UV-C radiation for exemplary purposes, but other radiation source wavelengths may also be employed. In some variations, the method may involve generating a time-based cycle, followed by checking at the end of the cycle if a predetermined threshold dose was reached. In certain embodiments utilizing a time-based cycle, the process time is selected to achieve delivery of an acceptable threshold (e.g., minimum) total dose of disinfecting radiation within one or more disinfection zones within the disinfection chamber. For example, where UV-C radiation is used as the disinfecting radiation, a primary timed interval for the disinfection cycle may be determined by taking into account the intensity of UV-C radiation delivered to one or more disinfecting regions within the disinfection chamber and calculating a time required to deliver a total dose of UV-C radiation selected from between about 50,000 $\mu J/cm^2$ and about 10,000,000 $\mu J/cm^2$. In certain such embodiments, a primary timed interval may be determined by calculating the time required to deliver a total dose of UV-C radiation selected from between about 50,000 $\mu J/cm^2$ and about 1,000,000 $\mu J/cm^2$, such as, for example, a dose selected from between about 50,000 $\mu J/cm^2$ and about 750,000 $\mu J/cm^2$, between about 50,000 $\mu J/cm^2$ and about 650,000 $\mu J/cm^2$, between about 50,000 $\mu J/cm^2$ and about 500,000 $\mu J/cm^2$, between about 50,000 $\mu J/cm^2$ and about 450,000 $\mu J/cm^2$, between about 50,000 $\mu J/cm^2$ and about 350,000 $\mu J/cm^2$, between about 50,000 $\mu J/cm^2$ and about 250,000 $\mu J/cm^2$, and between about 50,000 $\mu J/cm^2$ and about 100,000 $\mu J/cm^2$ or between other like values. In further such embodiments, a time-based cycle may be determined by calculating the time required to deliver a total dose of UV-C radiation selected from between about 150,000 $\mu J/cm^2$ and about 750,000 $\mu J/cm^2$, between about 150,000 $\mu J/cm^2$ and about 650,000 $\mu J/cm^2$, between about 150,000 $\mu J/cm^2$ and about 500,000 $\mu J/cm^2$, between about 150,000 $\mu J/cm^2$ and about 450,000 $\mu J/cm^2$, between about 150,000 $\mu J/cm^2$ and about 350,000 $\mu J/cm^2$, and between about 150,000 $\mu J/cm^2$ and about 250,000 $\mu J/cm^2$ or between other like values. In still further such embodiments, a primary timed interval may be determined by calculating the time required to deliver a total dose of UV-C radiation selected from between about 250,000 $\mu J/cm^2$ and about 750,000 $\mu J/cm^2$, between about 250,000 $\mu J/cm^2$ and about 650,000 $\mu J/cm^2$, between about 250,000 $\mu J/cm^2$ and about 500,000 $\mu J/cm^2$, between about 250,000 $\mu J/cm^2$ and about 450,000 $\mu J/cm^2$, and between about 250,000 $\mu J/cm^2$ and about 350,000 $\mu J/cm^2$ or between other like values.

Within the devices and systems described herein, several different sources of variability can affect system performance. For example, UV-C source output may vary or drift over time, and specifically, where UV-C sources are used for the disinfecting radiation, lamp output can change with use, with the temperature of the operating environment, which can affect UV-C lamp performance (i.e., the intensity of UV-C light emitted), with surface cleanliness or a condition of the source (e.g., a UV-C lamp), and/or with the condition of the chamber's reflecting/re-radiating surfaces, which might reduce or affect in some undesirable way, the intensity of UV-C radiation reaching the one or more articles to be disinfected. Performance of the one or more UV-C sensors can also degrade or change over time or unexpectedly change due to a sensor failure, contamination, misalignment, and the like. Embodiments of the devices and systems described herein generate one or more disinfecting regions within a disinfecting chamber, and placement of the one or more articles, especially when accomplished by a human operator, can be inconsistent. Placement inconsistency is one factor that can affect the intensity or total dose of UV-C radiation delivered to the articles.

In particular embodiments described herein, a system monitoring and control algorithm operates to regularly determine the status of the one or more UV-C sources. The algorithm may selectively calibrate each of the one or more UV-C sources and the one or more UV-C sensors. The calibration process may be performed on each source and each sensor individually, or the calibration process may be performed on one or more cooperating sources and sensors. The algorithm may further detect the presence, and in addition or in the alternative, the positioning of one or more articles within the disinfection chamber. Based on the status information gathered and/or calibration conducted by the system monitoring and control algorithm the from one or more of the various components of the disinfection systems, the system monitoring and control algorithm may further operate to perform one or more of the following acts: 1) alert a user to an error condition (e.g., a UV-C source or a UV-C sensor that is not functioning within a selected operational specification); 2) adjust the targeted process time for the one or more articles to be disinfected; and 3) alter the operation of one or more components to ensure high-level disinfection within the predetermined cycle time (e.g., by modulating the output of the one or more UV-C sources).

In some embodiments, a system monitoring and control algorithm utilized in a system as described herein may monitor the times required to deliver sufficient energy for high level disinfection in the previous 5, 10, 15, 20, 25, 50, or other like number of disinfection cycles and vary the cycle time based on such information. In specific embodiments, based on an original or the most recent system calibration, the system may define a primary timed interval for a given article as 140 seconds. Using information collected from previous cycles, a system control algorithm might then increase or decrease the baseline in light of how long a selected number of previous disinfection cycles took to complete. Such an approach allows for adjustment of the primary timed interval based on component performance feedback, such as tube (i.e., radiation source) degradation. Alternatively, the primary timed interval may be initially programmed to last 140 seconds and then adjusted up or down based on an average of the time applied in the previous 20 cycles. In yet further variations, the method could begin with a primary timed interval (e.g., a 90 second cycle) and when that interval has elapsed, the dose every x seconds (e.g., every five seconds) could be checked to see if the predetermined dose is reached/exceeded. If the predetermined dose has been reached/exceeded, then the disinfection cycle would terminate.

The disinfection cycle can be monitored and controlled by the exemplary monitoring and control system 1150 illustrated in FIG. 11B. The system monitoring and control algorithm 1100 represented in FIG. 11A can be implemented and run in parallel with the system 1150 of FIG. 11B. For example, system parameters that enable proper function, such as lamp operation, lamp current/voltage, operating temperature range(s), status and operation of temperature sensors, status and operation of a temperature control system, presence of one or more articles to be disinfected, identity and provenance of said article, and status of chamber door interlocks can be monitored, and further may be controlled. In some variations of the algorithm 1100, a sensor monitoring a temperature of interest which could be somewhere within the chamber, on the surface of the probe being disinfected, or elsewhere, is sampled and readings added to a rolling buffer that contains N readings. Temperatures may be read, for example, every 800 milliseconds. The rolling average is compared to an allowed and predetermined temperature threshold maximum ($T_{max}$). When the average temperature is above the $T_{max}$, an error code may be generated and the system may be directed to go into wait mode until the temperature within the chamber drops below the maximum allowed value. The $T_{max}$ can be selected and adjusted based on the one or more articles to be disinfected. Depending on the one or more articles being disinfected, the $T_{max}$ may be selected from 45° C., 50° C., 55° C., and 60° C. or another like temperature value. For example, where the article to be disinfected is an ultrasound probe, the $T_{max}$ may be set at a temperature selected from a temperature falling within a range selected from 45° C.-55° C., 45° C.-50° C., 48° C.-50° C., and another like temperature range.

The exemplary monitoring and control system 1150 includes one or more processing units 1152. The processing unit 1152 of FIG. 11B may be a single processing unit such as a microprocessor or a microcontroller, or the processing unit 1152 may be a formation of multiple processing units. The processing unit 1152 may be or include one or more field programmable gate arrays (FPGA), application specific integrated circuits (ASIC), digital signal processors (DSP), central processing units (CPU), or other like devices. The processing unit 1152 of the disinfection devices presented may be broadly referenced herein as a CPU. That is, the processing unit 1152 may be one or more of a microprocessor, a microcontroller, an FPGA, an ASIC, a DSP, a CPU, a finite state machine, or some other control processor device.

Certain features of the exemplary monitoring and control system 1150 may be carried out with the cooperation of a memory device. The memory device may include one or more portions to store data, such as measurement collected from sensors and parameters used to control features of the system monitoring and control algorithm 1100. The memory device may also include one or more portions to store program instructions executable by the processing unit 1152. In some cases, one memory device stores both program instructions and data. In other cases, program instructions are stored in one memory device, and data is stored in a separate and distinct memory device. In FIG. 11B, a command table 1154 is formed in a first memory device to store program instructions, and a system parameter monitoring fault handling module 1156 is formed in a second memory device to store data. The first and second memory devices may be arranged in the same physical memory device, or the first and second memory devices may be arranged in different memory devices.

In FIG. 11B, the memory devices used to form command table 1154 and system parameter monitoring fault handling module 1156 may include any combination of volatile and non-volatile non-transitory computer-readable media (CRM) for reading and writing data. Volatile computer-readable media includes, for example, random access memory (RAM). Non-volatile computer-readable media includes, for example, read only memory (ROM), magnetic-based memory, phase change memory, flash memory, and the like. The memory devices may be formed within an integrated circuit locally external to the processing unit 1152, remotely external to the processing unit 1152, or in some combination.

The program instructions stored in command table 1154 may be a particular collection of software instructions executable by the processing unit 1152 in order to carry out functions of the system monitoring and control algorithm 1100. The software instructions may be stored individually or as groups of instructions in files. The files may include functions, services, libraries, and the like. The files may include one or more computer programs or may be part of a larger computer program. Alternatively or in addition, each file may include data or other computational support material useful to carry out the computing functions of the system monitoring and control algorithm 1100. The software instructions operatively configure hardware and other software in the system monitoring and control algorithm 1100 so that electronic data may be collected and communicated to provide high level disinfection in a disinfection device as described herein. The software instructions stored in command table 1154 configure the system monitoring and control algorithm 1100 to control radiation sources and to monitor radiation sensors. In some cases, a single processing unit 1152 executes software instructions from the command table 1154 to both control radiation sources and to monitor radiation sensors. In such a case, program instructions are executed serially, but since the program instructions are executed very quickly with respect to the time it takes for system parameters to change appreciably, it is considered that both operations (i.e., controlling radiation sources and monitoring radiation sensors) are executing in parallel. In other embodiments, two or more processing units within processing unit 1152 are executing software instructions, and both operations (i.e., controlling radiation sources and monitoring radiation sensors) are literally executing in parallel.

In some cases, the operation of the system monitoring and control algorithm 1100 is reconfigurable. That is, the operation of system monitoring and control algorithm 1100 may be arranged with one set of parameters and later rearranged with another set of parameters. The parameters may include the software instructions stored in the command table 1154. The parameters may also include system parameters stored in module 1156. The reconfiguration is arranged in some cases to be performed while the system is deployed, for example, after entry of certain parameter information.

The processing unit 1152 includes a time counting feature, which may be integrated within a CPU, formed with discrete components separate from a CPU, or formed with a combination of discrete components separate from the CPU and integrated components within the CPU. The time counting feature may be a clock generation circuit such as a phase locked loop, a resistor/capacitor (RC) circuit, a crystal based oscillator, or some other periodic signal generator. The time counting feature is configured to generate a periodic signal used as a counter or clock to accumulate and integrate radiation sensor samples, to carry out functions of the fixed time period (i.e., primary timed interval), to carry out functions of the predetermined time interval, and for other reasons. In some cases, the frequency of the time counting feature is configurable. For example, the frequency of a time count may be configured, the direction (i.e., count up or down) may be configurable, and other aspects of the time counting feature may be configurable.

The exemplary monitoring and control system 1150 includes a radiation source unit 1158, a radiation detection unit 1160, and a temperature measurement unit 1162. As described herein, the system monitoring and control algorithm 1100 controls and directs the radiation source unit 1158 to produce radiation (e.g., UV-C energy) according to particular parameters discussed herein. The system monitoring and control algorithm 1100 further takes radiation sample measurements with the radiation detection unit 1160 and temperature sample measurements with the temperature measurement unit 1162.

Certain optional features may also be arranged in the exemplary monitoring and control system 1150. For example, a radio frequency identification (RFID) reader 1170 may be included. The RFID reader 1170 may be useful to track articles that are placed within of the disinfection chamber. By automating a detection and identification process of articles to be disinfected, for example, an increased assurance that a particular article has been disinfected can be provided. In some embodiments, the status and results of a disinfection process can be electronically coupled to a system-wide unique RFID address. Such embodiments facilitate improved record keeping, compliance with government regulations, integrity of the article being disinfected, and many other aspects of disinfection. Another optional feature found in some embodiments is a printer 1172, which can facilitate accurate record keeping associated with each subject disinfection device. Yet one more optional feature in the exemplary monitoring and control system 1150 is a peripheral device 1176 configured to send, receive, or send and receive certain control or status information. The control or status information may take the form of commands, data, parameters, and the like. In some cases the control and status information is passed from the peripheral device 1176 to the system parameter monitoring fault handling module 1156; in some cases, the control and status information is communicated from the peripheral device 1176 to another device remote from the exemplary monitoring and control system 1150; and in yet other cases, the control and status information is passed in other directions to other devices.

The system monitoring and control algorithm 1100 may also include a temperature control logic that serves to operate a temperature control system in response to chamber temperatures detected by the temperature sensor 1162. Where included, a temperature control system is configured to help maintain the disinfection chamber within a selected temperature range during the entirety of each disinfection cycle. For instance, it has been found that sources of UV-C radiation 1158, such as light tubes generating UV-C radiation, work with acceptably higher efficiency when at a temperature of between about 35° C. and about 45° C. The temperature control system 1164 may optionally include, for example, one or more cooling units (e.g., fans) and/or one or more sources of heat. In certain embodiments, the temperature control system 1164 may be programmed such that the one or more fans turn on to cool the disinfection chamber when the temperature therein exceeds, for example, about 50° C., about 45° C., about 40° C., about 35° C., and about 30° C., or about another like temperature, and the one or more sources of heat are utilized to warm the disinfection chamber if the temperature within the chamber falls below a temperature selected from, for example, about 35° C., about 30° C., and about 25° C., or about another like temperature. The temperature control algorithm may also consider the rate of increase of temperature in combination with the current temperature measured by one or more temperature sensors 1162, along with the time remaining for the current disinfection cycle. In yet further variations, the system monitoring and control algorithm 1100 may periodically check the functioning status of the UV-C radiation sensors 1160 and UV-C radiation sources 1158 (e.g., minimum voltage to activate the sources, current travelling through the sources, cycle-specific and cumulative duration of use of the sources, etc.), and operate optional chamber door locks 1166 with the cooperation of data from optional door sensors 1174.

The systems employed herein effectively monitor a disinfection cycle duration to terminate the disinfection cycle at a cycle time that results in a lower threshold (e.g., minimum) but sufficient exposure dosage of disinfecting radiation to quickly and adequately disinfect the target article, while avoiding overexposure of said target article to the disinfecting radiation concomitant with elevated target article temperatures. For many polymeric materials commonly used in construction of, for example, medical devices or devices used in medical procedures, repeated over exposure can damage the article, and potential degradation can be more pronounced and exacerbated when the target article is heated to higher temperatures, such as in excess of 50° C., while concurrently being exposed to UV-C radiation. Thus it is beneficial to limit the temperatures reached within the disinfection chamber.

In order to confirm the intensity of the disinfecting radiation delivered to the one or more articles positioned within the disinfection chamber, assess the extent to which shadowing may occur, and confirm the process times that achieve delivery of a targeted minimum dose of disinfecting radiation, the devices and systems described herein may be configured to facilitate routine calibration. In specific embodiments, the systems are configured to allow assessment the irradiance and/or total dose of disinfecting radiation delivered to a central portion of one or more disinfecting regions, which in turn allows or drives appropriate adjustment to the system cycle times to better direct a threshold dose of disinfecting radiation be delivered to the one or more articles being disinfected. In certain such embodiments, during a calibration step, a calibration sensor 1168 (such as a UV-C sensor where UV-C radiation is used) is positioned within a disinfection region and the irradiance and/or total dose of disinfecting radiation is assessed. Assessment of the disinfecting radiation delivered to one or more disinfection regions may take place over any selected period of time, including for example, a fraction of a targeted cycle time, a full cycle time, or over multiple (e.g., 5, 10, 20, 30, 40, 50, or more) cycles. Based on the irradiance level and/or total dose of disinfecting radiation received by the calibration sensor 1168, operation of the disinfection system may be adjusted to account for deviations in the selected targeted total dose or irradiance. For example, operating at a lower threshold irradiance (e.g., a minimum) may still allow a sufficient total dose of disinfecting radiation to be delivered within a given disinfection cycle time. Where the irradiance is below the threshold, the cycle time may be increased to achieve the targeted total dose of disinfecting radiation, and where the irradiance is above the threshold, the cycle time may be decreased to achieve the targeted total dose of disinfecting radiation.

In particular embodiments, the irradiance level and/or total dose of disinfecting radiation delivered to the calibrating sensor 1168 is compared to the same values detected by the one or more disinfecting radiation sensors 1160 included in the disinfection chamber. Such a comparison allows the values detected by the calibration sensor 1168 to be correlated to the values detected by the one or more sensors 1160 included in the disinfection chamber, and the system calibrated using the difference(s) between the disinfecting radiation reading(s) by the calibration sensor 1168 and the readings(s) by the one or more sensors 1160 of the disinfection chamber. Calibrating the system in this way enables the system and/or its operator to, for example, account for system to system variability as well as variability in the amount of disinfecting radiation emitted and detected within the disinfection chamber.

The calibrating sensor 1168 may be associated with a positioning assembly, and the disinfection chamber may be configured to receive the positioning assembly so that the placement of the calibrating sensor 1168 within the disinfection chamber is precise and repeatable. If the disinfection chamber is configured to include two or more disinfection regions, each disinfection region may be provided with or be configured to receive a calibration sensor positioning assembly. In embodiments where the disinfection chamber is configured to include a single disinfection region, the disinfection chamber may be provided with or be configured to receive a single calibration sensor positioning assembly.

In particular embodiments, the calibration sensor positioning assembly may be removably mounted within the disinfection chamber at a defined, constant location within a disinfection region. For example, a calibration sensor positioning assembly may be removably mounted such that the calibration sensor is repeatably positioned in the same location and in the same attitude within the disinfection chamber. In certain embodiments, the positioning assembly and disinfection chamber may be configured to position the calibration sensor 1168 centrally within a disinfection region. Additionally the calibration sensor positioning assembly may be permanently or removably mounted to the calibration sensor 1168. Any suitable device may be used as a positioning assembly for a calibration sensor 1168. For example, the positioning assembly may be a bracket to which the calibration sensor 1168 can be affixed and that is configured to enable positioning of the bracket in a defined location within the disinfection chamber. In such embodiments, the bracket may be mounted or otherwise positioned within the disinfection chamber using, for example, one or more pins, bolts or screws. In addition, or as an alternative, a positioning bracket for a calibration sensor 1168 may include a location feature or surface that is keyed to fit within a mounting seat provided by the disinfection chamber. Such a mounting seat may also serve to position the one or more articles to be disinfected within the disinfection chamber, and where provided, a suspension assembly used to position the one or more articles to be disinfected may also include a location feature or surface keyed to the mounting seat. A mounting seat and keyed positioning assembly or suspension assembly can take on any selected or selectable configuration that permits removable mounting of the positioning assembly or suspension assembly within the disinfection chamber and brings the positioning assembly or suspension assembly into physical communication with the disinfection chamber. For example, the mounting seat and keyed positioning assembly may be configured as threaded connectors or male/female connectors that operate to maintain the positioning assembly in a defined position by, for example, a friction-fit, a twist lock, pinned, tapered, or press-fit connection. Providing a positioning assembly for the calibration sensor 1168 and configuring the disinfection chamber to provide for precise, reproducible placement and repositioning of the calibration sensor 1168 within the disinfection chamber facilitates reliable assessment of the intensity and dose of disinfecting radiation received by the one or more articles being disinfected.

Certain communication protocols are illustrated in FIG. 11B for passing data signals, control signals, or data and control signals between modules of the exemplary monitoring and control system 1150. The illustrated communication paths and protocols are illustrative and different communication paths and protocols may also be implemented. A serial peripheral interface (SPI) bus is illustrated between the processing unit 1152 and each of the measurement units (i.e., radiation sensor 1160 and temperature sensor 1162). Three other serial bus communication protocols are also illustrated in FIG. 11B. The calibration sensor 1168 and the optional printer 1172 are coupled to the processing unit 1152 via universal serial bus (USB) links, the optional RFID reader 1170 is coupled to the processing unit 1156 via an RS-485 serial bus link, and RS-232 serial communication links are also provided. In addition to serial communications, the processing unit 1152 may also communicate with additional optional devices over an Ethernet bus and a video graphics array (VGA) bus. The Ethernet bus or other similar network communication interface may be used to communicatively couple the exemplary monitoring and control system 1150 to certain remote computing devices or other exemplary monitoring and control systems 1150 so that data or control information may be passed bi-directionally. The VGA bus or another like interface may be used to couple a display-type device to the exemplary monitoring and control system 1150.

Figure 12A:
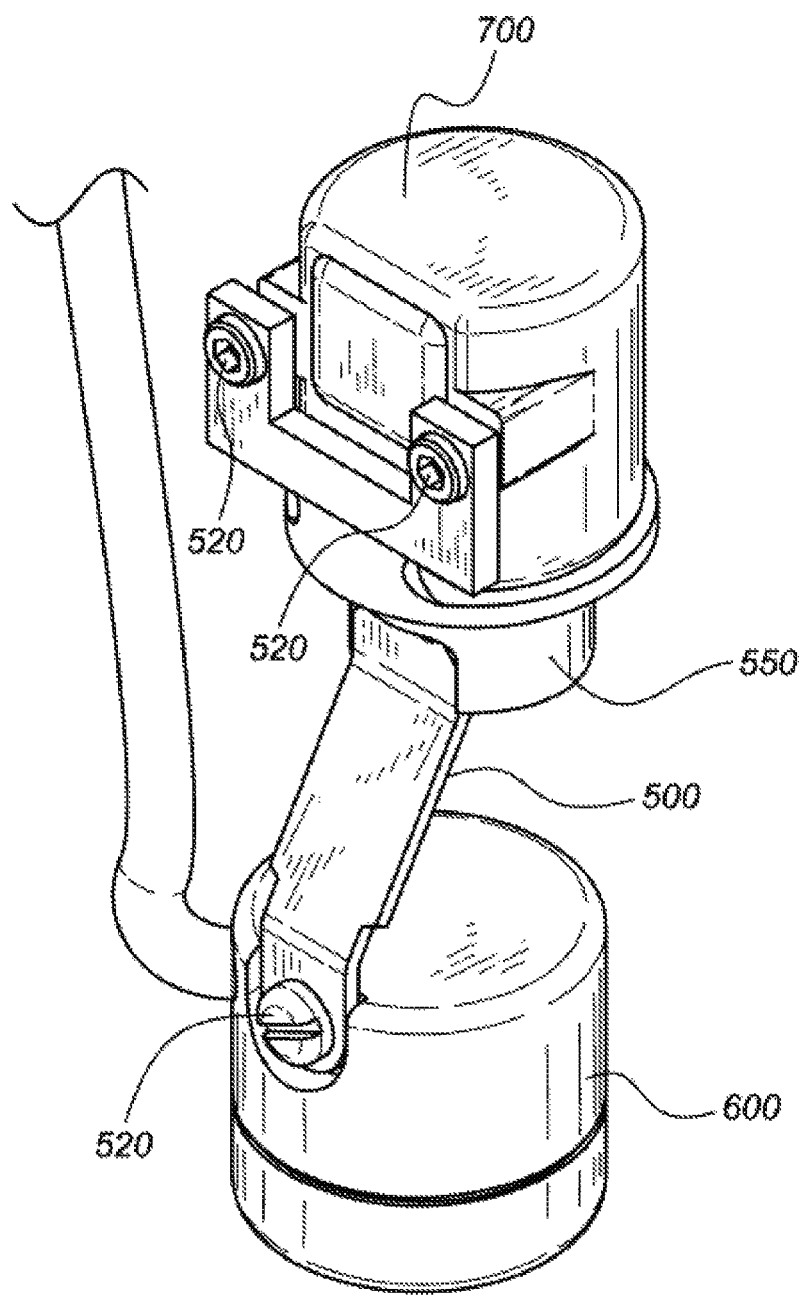
FIGS. 12A-12B illustrate an example of a positioning assembly according to the present description for reproducibly locating a calibration sensor within a disinfection chamber.
Figure 12B:
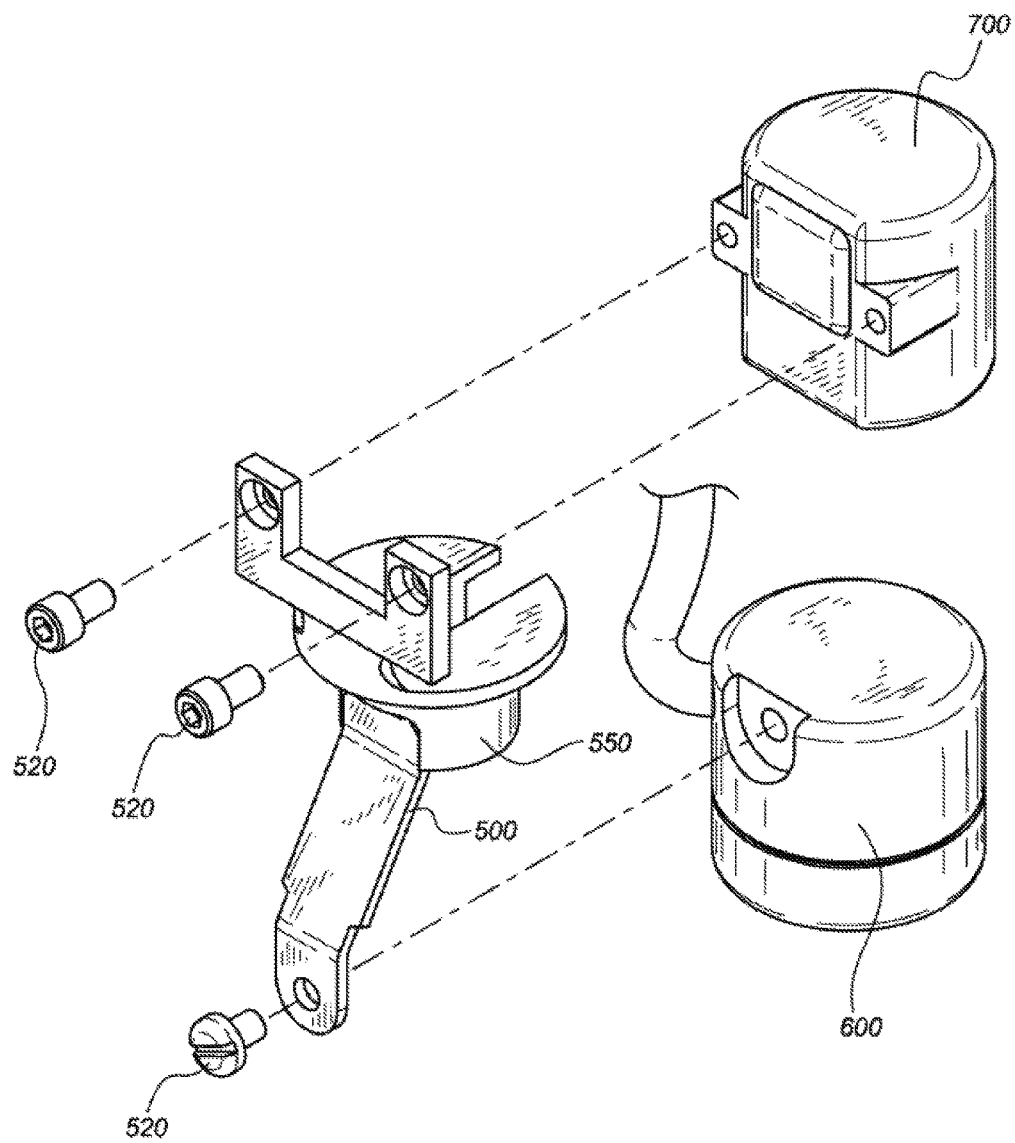

One embodiment of a positioning assembly for a calibration sensor according to the present description is illustrated in FIG. 12A and FIG. 12B. In the embodiment illustrated in these figures, the positioning assembly 1202 is a bracket to which a calibration sensor 1204 can be mounted. Optionally, in addition to the calibration sensor 1204, a traceability component, such as an RFID collar 1206, is included. The traceability component can be used to identify an associated calibration sensor 1204, to collect information regarding the status and/or cumulative uses of the calibration sensor 1204, to collect data for governmental compliance, and for other reasons.

FIG. 12B is an exploded view of the positioning assembly 1202, calibration sensor 1204, and optional traceability component 1206. As can be readily appreciated by reference to FIG. 12B, the calibration sensor 1204 and the optional traceability component 1206 can be mounted to the positioning assembly 1202 via any suitable connection mechanism, including one or more bolts 1208 that thread or otherwise pass through the positioning assembly 1202 and into the calibration sensor 1204 and optional traceability component 1206. The positioning assembly 1202 includes a positioning ring 1210 that provides a location surface keyed to a mounting seat provided in the disinfection chamber. In the embodiment illustrated in FIG. 12A and FIG. 12B, the positioning ring 1210 mates with a complimentary mounting seat provided within the disinfection chamber or, for example, through one of the one or more walls of the disinfection chamber, making it possible to accurately and reproducibly position and reposition the calibration sensor at a defined location within the disinfection chamber. Though FIG. 12A and FIG. 12B illustrate a positioning assembly as contemplated herein, it is to be understood that the positioning assembly shown in these figures is only one embodiment provided to illustrate a configuration of a positioning assembly that can be used in conjunction with a disinfection system according to the present description. From the detailed description provided herein, one of skill in the art will appreciate that a positioning assembly as described herein can be configured in many different ways to suit a variety of contexts and a variety of different disinfection systems.

II. Methods

Methods according to the present description are carried out rapidly, at low temperature, and provide high-level disinfection. The methods described herein include providing an article to be disinfected, positioning the article in a disinfection device, and carrying out a disinfection cycle, which can be accomplished in a short period of time. Generally, disinfection processes that are conducted more rapidly and at lower temperatures are desirable because many articles, including medical devices, are made from materials (e.g., plastics) that may physically or chemically degrade when exposed to disinfecting conditions, including exposure to UV radiation or high temperatures. Shortening the time of a disinfection cycle and maintaining an acceptably low temperature serve to preserve the long-term physical and chemical integrity of the articles being disinfected.

As described herein, a disinfection method carried out in a short period of time refers to a method wherein high-level disinfection is achieved within 10 minutes (i.e., 600 seconds or less). In particular embodiments, the methods described herein are carried out in less than ten minutes. For example, in some embodiments, the methods described herein achieve high-level disinfection within a time period selected from 600 seconds, 540 seconds, 480 seconds, 420 seconds, 360 seconds, 300 seconds, 240 seconds, 180 seconds, 120 seconds, 100 seconds, 90 seconds, 60 seconds, 45 seconds, 30 seconds, 15 seconds, and 10 seconds or within another like time. As described herein a device for carrying out a disinfection cycle can be configured for manual, semi-automatic, or automatic operation. Where configured for automatic or semi-automatic operation, the disinfection device may be configured to automatically terminate the disinfection cycle when a defined set of conditions is met.

The temperature within the disinfection chamber is maintained at a low level. One or both of the ambient temperature within the disinfection chamber or the surface temperature of the article to be disinfected is monitored. Whether the temperature monitored is a surface temperature of the article being disinfected or an ambient temperature within the disinfection chamber in general, embodiments of the disinfection system are operated such that the temperature does not exceed 55° C. For example, in certain embodiments, the methods described herein include monitoring an ambient temperature or surface temperature of the article, and the disinfection system is operated and/or controlled such that the ambient or surface temperature measured does not exceed a temperature selected from 35° C., 40° C., 50° C., and 55° C. or another like temperature. Where the surface temperature of the article and/or the ambient temperature of the disinfection chamber exceeds the selected threshold, the disinfection may be paused or terminated as described herein.

The intensity of disinfecting radiation delivered within the disinfection chamber of the devices and systems described herein facilitates rapid, low temperature disinfection. In particular embodiments, methods according to the present description include delivering high intensity UV-C radiation to the one or more articles to be disinfected. In such embodiments, the UV-C radiation may be delivered to the one or more articles to be disinfected at an irradiance level of at least about 1,500 $\mu W/cm^2$. In certain embodiments, one or more disinfection regions are created within the disinfection chamber, and within each of the one or more disinfection regions, UV-C radiation is delivered at an irradiance level of at least about 1,500 $\mu W/cm^2$. For example, the irradiance of the UV-C radiation delivered to the one or more disinfection regions may range from an irradiance level of at least about 1,500 $\mu W/cm^2$ and up to about 5,000 $\mu W/cm^2$. In further embodiments, the one or more UV-C source(s) may be selected and arranged to provide one or more disinfecting regions within the disinfection chamber wherein the minimum irradiance level of the UV-C radiation delivered to one or more articles to be disinfected is selected from between about 1,500 $\mu W/cm^2$ and about 2,000 $\mu W/cm^2$, between about 1,500 $\mu W/cm^2$ and about 2,500 $\mu W/cm^2$, between about 1,500 $\mu W/cm^2$ and about 3,000 $\mu W/cm^2$, between about 2,000 $\mu W/cm^2$ and about 2,500 $\mu W/cm^2$, between about 2,000 $\mu W/cm^2$ and about 3,000 $\mu W/cm^2$, between about 2,000 $\mu W/cm^2$ and about 3,500 $\mu W/cm^2$, between about 2,000 $\mu W/cm^2$ and about 2,500 $\mu W/cm^2$, between about 2,000 $\mu W/cm^2$ and about 2,750 $\mu W/cm^2$, between about 2,500 $\mu W/cm^2$ and about 2,600 $\mu W/cm^2$, between about 2,500 $\mu W/cm^2$ and about 2,750 $\mu W/cm^2$, and between about 2,500 $\mu W/cm^2$ and about 3,000 $\mu W/cm^2$ or between other like irradiance level ranges.

Embodiments of the methods described herein may include creating a disinfection region within a disinfection chamber, positioning an article to be disinfected within the disinfection region, and delivering high intensity UV-C radiation to the disinfection region, wherein the high intensity UV-C radiation is sufficient to achieve high-level disinfection within a time interval as detailed herein. In such embodiments, the intensity of the UV-C radiation delivered to the disinfection region may be selected from the values and ranges described herein. Additionally, it is to be understood that the methods described herein may include creating two or more disinfection regions within a disinfection chamber as described herein, positioning at least one article to be disinfected within each of the two or more disinfection regions, and delivering high intensity UV-C radiation as described herein to each of the disinfecting regions.

The dose of UV-C radiation within the disinfection chamber is also monitored. In methods according to the present description, the UV-C radiation dose can be used in different ways to define a disinfection process. In particular embodiments, a disinfection process as described herein proceeds for a predetermined time selected to deliver a threshold dose of UV-C radiation to one or more articles, following which, the UV-C dose delivered to the one or more articles is assessed. Depending on the UV-C dose delivered during the first time interval, the system may continue the disinfection process for a second time interval calculated to ensure sufficient UV-C radiation has been dosed in order to achieve high-level disinfection. In order to assess the UV-C dose delivered to the article at or after the first time interval, one of several approaches may be taken. For example, the average UV-C dose of each of the sensors included in the disinfection chamber might be assessed in combination with the specific dose of UV-C radiation for at least one of the sensors. Alternatively, the UV-C exposure might be assessed simply by an average of UV-C exposure over all sensors or a set of sensors, or by assessment of the specific UV-C exposure at each sensor. In specific embodiments, the threshold (e.g., minimum) doses of UV-C radiation may be selected from those detailed herein. For instance, where the specific UV-C exposure is monitored at one or more sensors or an average UV-C radiation exposure is monitored across two or more sensors, threshold doses for such specific or average UV-C doses may be selected from between about 50,000 $\mu J/cm^2$ and about 10,000,000 $\mu J/cm^2$ or within another like range. In such embodiments, the dose may be selected from between about 50,000 $\mu J/cm^2$ and about 1,000,000 $\mu J/cm^2$, such as, for example, a dose selected from between about 50,000 $\mu J/cm^2$ and about 750,000 $\mu J/cm^2$, between about 50,000 $\mu J/cm^2$ and about 650,000 $\mu J/cm^2$, between about 50,000 $\mu J/cm^2$ and about 500,000 $\mu J/cm^2$, between about 50,000 $\mu J/cm^2$ and about 450,000 $\mu J/cm^2$, between about 50,000 $\mu J/cm^2$ and about 350,000 $\mu J/cm^2$, between about 50,000 $\mu J/cm^2$ and about 250,000 $\mu J/cm^2$, and between about 50,000 $\mu J/cm^2$ and about 100,000 $\mu J/cm^2$ or within another like range. In further embodiments, the dose may be selected from between about 150,000 $\mu J/cm^2$ and about 750,000 $\mu J/cm^2$, between about 150,000 $\mu J/cm^2$ and about 650,000 $\mu J/cm^2$, between about 150,000 $\mu J/cm^2$ and about 500,000 $\mu J/cm^2$, between about 150,000 $\mu J/cm^2$ and about 450,000 $\mu J/cm^2$, between about 150,000 $\mu J/cm^2$ and about 350,000 $\mu J/cm^2$, and between about 150,000 $\mu J/cm^2$ and about 250,000 $\mu J/cm^2$ or within another like range. In still further such embodiments, the dose may be selected from between about 250,000 $\mu J/cm^2$ and about 750,000 $\mu J/cm^2$, between about 250,000 $\mu J/cm^2$ and about 650,000 $\mu J/cm^2$, between about 250,000 $\mu J/cm^2$ and about 500,000 $\mu J/cm^2$, between about 250,000 $\mu J/cm^2$ and about 450,000 $\mu J/cm^2$, and between about 250,000 $\mu J/cm^2$ and about 350,000 $\mu J/cm^2$ or within another like range.

For a given disinfection system, methods for determining disinfection cycle times are also provided. First, an initial target dose of disinfecting radiation (e.g., UV-C radiation) to achieve high level disinfection for a selected article is determined. This act involves assessing UV-C exposure required to achieve a selected logarithmic kill performance for selected pathogens in controlled conditions outside the disinfection system. The disinfection conditions determined outside the disinfection system are determined in-situ and are used to provide first approximation of the disinfecting radiation dose that will achieve high-level disinfection.

The first approximation of the dose of disinfecting radiation required for a selected logarithmic reduction in pathogens is then used to set the disinfection cycle parameters, including an initial disinfection cycle time, for the disinfection system. Using such an approach, the initial target dose information can be confirmed in a disinfection system according to the present description, and the disinfection cycle parameters adjusted, if needed, to achieve a selected logarithmic reduction in pathogens at a lower cycle time and/or a reduced exposure to disinfecting radiation. It is to be recognized that the characteristics of disinfection devices can vary. Therefore, for each different disinfection device, the disinfection cycle parameters applied to achieve an experimentally determined first approximation dose of UV-C radiation outside of the device may vary from one device to another as they are applied to any given device.

A predetermined disinfection exposure to achieve a targeted first approximation dose of disinfecting radiation will, within a given device, depend on, and will be adjusted in recognition of, among other factors, the nature, number, positioning, and output of the one or more UV-C radiation sources; the position, location, geometry and reflective nature of the walls or surfaces that define the chamber; and the number and positioning of the UV-C sensors—all of which serve to define the intensity level of the UV-C radiation delivered to the one or more articles to be disinfected. Likewise the location of the one or more articles to be disinfected may affect the efficacy of the intended disinfection.

As used herein, a "dose" may be determined as the integral of the irradiance of the one or more UV-C sources over the time period during which an article is subjected to the defined irradiance. The lowest disinfection cycle time for a given set of system characteristics is identified as the primary timed interval. As detailed herein, a disinfection system as described herein may be programmed to utilize one or more algorithms, such as a system monitoring and control algorithm that processes current and historic system information (shadowing, tube and sensor degradation, temperature, etc.) to adjust the primary timed interval as needed to achieve a selected logarithmic reduction in pathogens. In specific embodiments, disinfection systems as described herein are programmed to adjust the primary timed interval, as needed, to achieve high-level disinfection.

In one example of a method for determining the target cycle times for a disinfection device, one or more log-reduction kill tests are conducted in-situ. The log-reduction kills tests operate by irradiating materials having known pathogen counts distributed over a fixed area, of several different pathogens (e.g., live bacteria, spores, fungi, molds, viruses) deposited on substrates. The one or more pathogens can be combined in a single test on a single substrate, or the tests can be run individually for each pathogen, and any suitable substrate can be used. In certain embodiments, the substrate is glass, such as a glass slide or a Petri dish. Moreover, the pathogen(s) can be provided within or in combination with one or more interfering media designed to approximate the contamination typically seen in the articles to be disinfected. Once the substrate has been inoculated with the pathogen, at a known population, appropriately distributed over a fixed area, the substrate is irradiated directly, and the incident radiance is measured at the plane of the substrate. The radiation source can be chosen based on the source used in the disinfection system and the radiation delivered can be tailored to approximate the intensity level produced in the disinfection system. For example, if the disinfection system utilizes a UV-C radiation source, the radiation source used in the in-situ kill test will radiate UV-C in the same power spectrum. Optical filters may also be employed to ensure the chosen radiation accurately mimics the radiation used in the actual system. Substrates inoculated with known populations of pathogens will then be subjected to a predetermined intensity of UV-C radiation to identify the exposure (time or total dose of UV-C radiation delivered) required to achieve a selected log-reduction in population of surviving pathogen(s). In some embodiments, the log-reduction kill test can be conducted to provide a logarithmic kill versus time of exposure scale (a "kill curve"). Using this information generated outside a disinfection system allows rank-ordering of pathogen susceptibility to disinfecting conditions (e.g., UV-C exposure), as well as assessment of the potential effect of interfering agents or media that may be added to the inoculating matrix. Such interfering agents may impede light penetration, or may protect the pathogen in some way, and may be used to simulate the presence of biological substances found in situ. The logarithmic kill times achieved in the log-reduction kill tests provide a first approximation to the target dose.

Using the first approximation target dose information, logarithmic kill assays are then repeated, this time in the disinfection system itself using the one or more articles to be disinfected (e.g., an ultrasound or endotracheal probe). In this step, the surface of the article itself may be directly inoculated to achieve a known pathogen load or population distributed over a fixed area. In an alternative embodiment, a test carrier-substrate may be treated and positioned within a disinfection chamber within a disinfection region. In some such embodiments, the test carrier substrate can be affixed to the surface of the article to be disinfected. The use of a test substrate instead of, for example, inoculating the surface of an article to be disinfected, may speed turn-around times required to assess the target process time and UV-C dose information. A test substrate may also better facilitate reproducible recovery of pathogen(s) post-exposure. Pathogen kill efficiency is again assessed across a range of UV-C exposures—(total UV doses), with the exposures being set based on the disinfection system characteristics and the first approximation to the target dose. The range of exposure times may start, for example, at 30 seconds or below and continue up through several minutes, including up to tens of minutes. Logarithmic pathogen kill curves are then calculated and compared with the first approximation target dose information. Using the kill curve from the testing conducted in the disinfection system itself, a new target dose and disinfection cycle time are established, and may be further modified in consideration of other safety factors, to provide the primary timed interval (and other process parameters) for the disinfection system. Using the methods described herein, for a given system, disinfection cycle times can be reduced and more accurately targeted to the articles to be disinfected and the pathogens to be eliminated.

Alternatively, a method for determining the target cycle times for a given article and/or level of contamination can be conducted using the device in which the articles to be disinfected will processed. In such a method, instead of conducting the testing required to arrive at a first approximation dose of UV-C radiation using an instrument other than the disinfection device, the same process can be carried out within device itself. The same process as already described can be carried out to produce logarithmic pathogen kill curves and select a first approximation process time or minimum UV-C dose. Advantageously, the methods described for determining a process time and/or low UV-C dose needed to achieve a selected level of disinfection can be modified or altered to fit various different contamination scenarios (e.g., nature and concentration of pathogens, presence of biologic fluids or other biologic material, etc.). Where a given primary timed interval is determined to achieve a selected level of disinfection in a given disinfection device, the total UV-C represented achieved by such process time can be extrapolated and used as a minimum dose for management of the disinfection system, such as by a system control algorithm.

In one embodiment, once a primary timed interval in a given disinfection device has been identified as producing high-level disinfection, a UV-C detector can be positioned within the disinfection device in the same location as the test article that was disinfected, and several test disinfection cycles can be carried out at the identified process time. The total UV-C dose detected by the UV-C detector during each test run can be identified and these measurements can be processed to confirm the targeted UV-C dose suitable for achieving the selected level of disinfection. In even further embodiments, the time determined to achieve a selected dose of UV-C radiation can be adjusted to take into account one or more operating variables, including, for example, known margins of error for the one or more UV-C sensors utilized, the variability in UV-C radiation emitted from the one or more UV-C sources, and possible levels of contamination present on various articles to be disinfected or on reflective surfaces comprised in the chamber. The selected primary timed interval and targeted total UV-C dose detected by the system can also be adjusted to account for possible shadowing within the disinfection chamber when one or more articles are present and to provide for a selected safety margin.

As used herein, the term "module" refers to an electronic circuit, a processor unit (e.g., shared, dedicated, group, single core, multicore, or the like) and memory operative to execute one or more software or firmware programs, an application specific integrated circuit (ASIC), a combinational logic circuit, or some other individual or cooperative coupling of suitable components (either hardware or software) that provides the functionally described with respect to the module.

In the foregoing description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with electronic and computing systems including client and server computing systems, as well as networks have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, e.g., "including, but not limited to."

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the context clearly dictates otherwise. It should also be noted that the term "or" is generally employed as including "and/or" unless the context clearly dictates otherwise.

As used herein, the term "about" or "approximately" when used in conjunction with a number refers to any number within 1, 5 or 10% of the referenced number.

The headings and Abstract of the Disclosure provided herein are for convenience only and do not interpret the scope or meaning of the embodiments.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A disinfection method associated with an interior volume of a disinfection chamber, comprising:
   beginning a disinfection cycle to disinfect a medical device, the disinfection cycle spanning a fixed time period, the fixed time period including two or more sequential predetermined time intervals;
   delivering a dose of disinfecting radiation to the medical device;
   reading at least one value representing an amount of radiation received by at least one measurement sensor during each predetermined time interval;
   reading at least one value representing an amount of radiation received by at least one reference sensor during each predetermined time interval;
   filtering values read from the at least one measurement sensor based on values read from the at least one reference sensor to produce conditioned values;
   calculate a radiation dose based on an accumulation of conditioned values;
   at the expiration of the fixed time period, determining whether or not the radiation dose has crossed a first threshold, the first threshold indicating a sufficient dose of radiation;
   ending the disinfection cycle if the radiation dose has crossed the first threshold;
   if the radiation dose has not crossed the first threshold, determining whether or not the radiation dose has crossed a second threshold, the second threshold indicating a lower dose of radiation;
   ending the disinfection cycle if the radiation dose has not crossed the second threshold; and
   based on any detected errors, selectively extending or ending the disinfection cycle if the radiation dose has crossed the second threshold.

2. A disinfection method according to claim 1, wherein upon ending the disinfection cycle because the radiation dose has crossed the first threshold, the method further comprising:
   outputting a disinfection success indication.

3. A disinfection method according to claim 1, wherein upon ending the disinfection cycle because the radiation dose has not crossed the second threshold, the method further comprising:
   outputting a disinfection failure indication.

4. A disinfection method according to claim 1, wherein at least one detected error includes a previous extension of the disinfection cycle.

5. A disinfection method according to claim 1, wherein at least one detected error includes an elevated temperature in the disinfection chamber.

6. A disinfection method according to claim 1, further comprising:
   concurrent with the disinfection cycle, monitoring at least one condition sensor that provides one or more of door lock data, temperature data, temperature control system data, electronic identification data, and radiation source data.

7. A disinfection method according to claim 6, wherein selectively extending or ending the disinfection cycle if the radiation dose has crossed the second threshold is based at least in part on data from the at least one condition sensor.

8. A disinfection method according to claim 6, comprising:
   based on data collected as a result of monitoring the at least one condition sensor, directing an immediate end of the disinfection cycle.

9. A disinfection method according to claim 1, wherein the fixed time period is a selectable value between 10 seconds and 600 seconds.

10. A disinfection method according to claim 1, wherein the dose of disinfecting radiation is a dose of UV-C radiation.

11. A disinfection device, comprising:
    a disinfection chamber having an interior volume in which to arrange at least one medical device to be disinfected;
    a first timing module to govern a disinfection cycle that will deliver a dose of disinfecting radiation to the medical device, the disinfection cycle spanning a fixed time period, the fixed time period including two or more sequential predetermined time intervals;
    a second timing module to govern each sequential predetermined time interval;
    a radiation source arranged to deliver the dose of disinfecting radiation to the medical device;
    at least one measurement sensor arranged to read at least one value representing an amount of radiation received during each predetermined time interval;
    at least one reference sensor arranged to read at least one value representing an amount of radiation received by during each predetermined time interval;
    a logic module having a processing unit and a memory, the logic module arranged to:
      condition values read from the at least one measurement sensor based on values read from the at least one reference sensor to produce conditioned values;
      determine a radiation dose based on an accumulation of conditioned values;
      at the expiration of the fixed time period, determine whether or not the radiation dose has crossed a first threshold, the first threshold indicating a sufficient dose of radiation, and end the disinfection cycle if the radiation dose has crossed the first threshold;
      if the radiation dose has not crossed the first threshold, determine whether or not the radiation dose has crossed a second threshold, the second threshold indicating a lower dose of radiation, and end the disinfection cycle if the radiation dose has not crossed the second threshold; and
      based on any detected errors, selectively extend or end the disinfection cycle if the radiation dose has crossed the second threshold.

12. A disinfection device according to claim 11, comprising:
    a first output arranged as a disinfection success indicator; and
    a second output arranged as a disinfection failure indicator.

13. A disinfection device according to claim 11, wherein a detected error includes at least one of a previous extension of the disinfection cycle and an elevated temperature in the disinfection chamber.

14. A disinfection device according to claim 11, further comprising:
    at least one input arranged to receive one or more of door lock data, temperature data, cooling fan data, electronic identification data, and radiation source data.

15. A disinfection device according to claim 11, further comprising:
    at least one input arranged to receive parameter data, the parameter data arranged to modify at least one of the fixed time period, the predetermined time interval, the first threshold, and the second threshold.

16. A non-transitory computer readable medium having executable software instructions thereon that, when executed, cause a processing unit to execute a disinfection device method, comprising:
- executing a calibration algorithm, the calibration algorithm configured to perform the acts of:
  - directing a radiation source to emit a calibration dose of disinfecting radiation into an interior volume of a disinfection chamber;
  - reading at least one value representing an amount of radiation received by at least one measurement sensor during delivery of the calibration dose of radiation;
  - reading at least one value representing an amount of radiation received by at least one reference sensor during delivery of the calibration dose of radiation; and
  - generating at least one calibration factor from data read by the at least one measurement sensor and data read by the reference sensor;
- executing a disinfecting algorithm to disinfect a medical device, the disinfecting algorithm configured to perform the acts of:
  - directing the radiation source to emit disinfecting radiation into the interior volume of the disinfection chamber over a fixed period of time;
  - detecting with the at least one measurement sensor an amount of disinfecting radiation within the interior volume of the disinfection chamber;
  - generating an accumulated radiation value, the accumulated radiation value representing an amount of radiation detected by the at least one measurement sensor, wherein at least some portion of the accumulated radiation value has the at least one calibration factor applied thereto;
  - after the fixed period of time expires, determining whether or not the accumulated radiation value has crossed a first threshold, the first threshold indicating a sufficient dose of radiation;
  - ending the disinfection algorithm e radiation dose has crossed the first threshold;
  - if the accumulated radiation value has not crossed the first threshold, determining whether or not the accumulated radiation value has crossed a second threshold, the second threshold indicating a lower dose of radiation;
  - ending the disinfection algorithm if the radiation dose has not crossed the second threshold; and
- concurrent with executing the disinfecting algorithm, executing a monitoring algorithm, the monitoring algorithm configured to perform the acts of:
  - receiving an open/closed status indication associated with an access opening to the disinfection chamber of the disinfection device; and
  - preventing the radiation source of the disinfection device from emitting radiation based on the open/closed status indication.

17. The non-transitory computer readable medium of claim 16 having executable software instructions thereon that, when executed, cause the processing unit to execute the disinfection device method, wherein executing the calibration algorithm includes:
- directing the radiation source to emit a calibration dose of disinfecting radiation into the interior volume of the disinfection chamber;
- reading at least one value representing an amount of radiation received by the at least one measurement sensor during delivery of the calibration dose of radiation;
- reading at least one value representing an amount of radiation received by the at least one reference sensor during delivery of the calibration dose of radiation; and
- generating the at least one calibration factor from data read by the at least one measurement sensor and data read by the reference sensor.

18. The non-transitory computer readable medium of claim 16 having executable software instructions thereon that, when executed, cause the processing unit to execute the disinfection device method, wherein executing the disinfecting algorithm includes:
- configuring a primary-timed-interval and a fixed-time-period;
- directing the radiation source to emit radiation over the fixed-time-period;
- updating the accumulated radiation value after an expiration of the fixed-time-period;
- if the accumulated radiation value does not reach a first radiation threshold, then re-directing the radiation source to emit radiation over the fixed-time-period; and
- detecting an expiration of the primary-timed-interval, and based on a comparison of the accumulated radiation value to the first radiation threshold, providing an indication of disinfection success or disinfection failure.

19. The non-transitory computer readable medium of claim 18 having executable software instructions thereon that, when executed, cause the processing unit to execute the disinfection device method, wherein executing the monitoring algorithm includes:
- operating a temperature control device, the temperature control device including at least one of a cooling device and a heating device.

20. The non-transitory computer readable medium of claim 19 having executable software instructions thereon that, when executed, cause the processing unit to execute the disinfection device method, wherein operating the temperature control device includes maintaining a temperature in the disinfecting chamber between about 35° C. and about 55° C.

* * * * *